(12) United States Patent
Homer

(10) Patent No.: US 8,594,951 B2
(45) Date of Patent: Nov. 26, 2013

(54) METHODS AND SYSTEMS FOR NUCLEIC ACID SEQUENCE ANALYSIS

(75) Inventor: Nils Homer, Arlington, MA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/363,697

(22) Filed: Feb. 1, 2012

(65) Prior Publication Data

US 2012/0197623 A1 Aug. 2, 2012

Related U.S. Application Data

(60) Provisional application No. 61/438,432, filed on Feb. 1, 2011, provisional application No. 61/505,631, filed on Jul. 8, 2011, provisional application No. 61/530,830, filed on Sep. 2, 2011.

(51) Int. Cl.
*G01N 33/50* (2006.01)
*G06G 7/58* (2006.01)

(52) U.S. Cl.
USPC .............................................. 702/20; 703/11

(58) Field of Classification Search
None
See application file for complete search history.

(56) References Cited

U.S. PATENT DOCUMENTS

| | | | |
|---|---|---|---|
| 7,424,371 | B2 | 9/2008 | Kamentsky |
| 2009/0053724 | A1 | 2/2009 | Roth et al. |
| 2010/0075327 | A1 | 3/2010 | Maxham et al. |
| 2011/0183320 | A1 | 7/2011 | Flusberg et al. |
| 2012/0035062 | A1 | 2/2012 | Schultz et al. |
| 2012/0109598 | A1 | 5/2012 | Davey et al. |

FOREIGN PATENT DOCUMENTS

| | | |
|---|---|---|
| WO | WO-2009117119 | 9/2009 |
| WO | WO-2011/156707 | 12/2011 |
| WO | WO-2012092515 | 7/2012 |

OTHER PUBLICATIONS

Brockman, William et al., "Quality scores and SNP detection in sequencing-by-synthesis systems", *Genome Research*, 18, 2008, 763-770.
Li, Heng et al., "Fast and accurate long-read alignment with Burrows-Wheeler transform", *Bioinformatics*, vol. 26 No. 5, 2010, 589-595.
Li, Heng et al., "Fast and accurate short read alignment with Burrows-Wheeler transform", *Bioinformatics*, vol. 25 No. 14, 2009, 1754-1760.
Lysholm, Fredrik et al., "FAAST: Flow-space Assisted Alignment Search Tool", *BMC Bioinformatics 2011*, 12:293, http://www.biomedcentral.com/1471-2105/12/293, 2011.
Ning, Zemin et al., "SSAHA: A Fast Search Method for Large DNA Databases", *Genome Res.*, 11:, 2001, 1725-1729.
Smith, T. F. et al., "Identification of Common Molecular Subsequences", *Journal of Molecular Biology*, 147, 10:, 1981, 195-197.
454 Sequencing System Software Manual Version 2.6, Part B: GS Run Processor, GS Reporter, GS Run Browser, GS Support Tool, (*last visited* May 2011), available at : http://genepool.bio.ed.ac.uk/Gene_Pool/454_software/Manuals/454SeqSys_SWManual-v2.6_PartB_May2011.pdf.
Li, Heng "Exploring single-sample SNP and INDEL calling with whole-genome de novo assembly", Bioinformatics, 28, 14:May 7, 2012, pp. 1838-1844.
Svantesson, Anna et al., "A mathematical model of the Pyrosequencing reaction system", *Biophysical Chemistry*, 100:2004, pp. 129-145.
PCT/US2011/067959 International Search Report and Written Opinion dated Nov. 16, 2012.
PCT/US2012/051361 International Search Report and Written Opinion dated Oct. 23, 2012.

*Primary Examiner* — Eric S DeJong
(74) *Attorney, Agent, or Firm* — Life Technologies Corporation

(57) ABSTRACT

Disclosed are new and improved methods and systems for nucleic acid sequence analysis that can analyze data indicative of natural by-products of nucleotide incorporation events without the need for exogenous labels or dyes to identify nucleic acid sequences of interest. In particular, the methods and systems of the present teachings can process such data and various forms thereof to align fragments of the nucleic acid(s) of interest, particularly those analyzed using an addition sequencing technique, for example, as occurs with the use of nucleotide flows.

17 Claims, 8 Drawing Sheets

```
SEQUENCE LISTING

<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 1
agtcaagcgt cccatg                                                    16
```

METHODS AND SYSTEMS FOR NUCLEIC ACID SEQUENCE ANALYSIS

RELATED APPLICATIONS

This application is related to U.S. Provisional Application No. 61/438,432 filed Feb. 1, 2011, which is incorporated herein by reference in its entirety and U.S. Provisional Application No. 61/505,631 filed Jul. 8, 2011, which is incorporated herein by reference in its entirety and U.S. Provisional Application No. 61/530,830 filed Sep. 2, 2011, which is incorporated herein by reference in its entirety.

FIELD

The present teachings relate to data analysis. More particularly, the present teachings relate to nucleic acid sequence analysis.

SEQUENCE LISTING

The instant application contains a Sequence Listing which has been submitted in ASCII format via EFS-Web and is hereby incorporated by reference in its entirety. Said ASCII copy, created on Mar. 15, 2012, is named LT00437US_Sequence_Listing_ST25.txt and is 558 bytes in size.

BACKGROUND

Today, various instruments, apparatus, and systems generate large volumes of data that require processing and analysis. Because a goal of many analytical techniques is high throughput and rapid analysis, not only should the analytical instrument operate efficiently to generate data, but the subsequent processing and analysis of the data also needs to be handled efficiently.

With respect to nucleic acid sequencing analysis, many known techniques rely on the use of exogenous labels and dyes to identify or recognize the incorporation of a nucleotide to a nucleic acid (polymer) or other chemical entity. However, such techniques can suffer inaccuracies, for example, where incorporation of a nucleotide with a label can be sterically hindered and suffer incomplete or inefficient incorporation. Consequently, techniques have been developed that can detect the natural by-products of transforming chemical reactions such as the incorporation of a natural nucleotide which produces a hydrogen ion. To that end, a sequencing instrument that is capable of electronically detecting nucleotide incorporation resulting from extension of a nucleic acid strand and can generate and output signals and data reflective of the relative hydrogen ion concentration associated with the nucleotide incorporation has been developed. See, e.g., U.S. Pat. No. 7,948,015 and U.S. Patent Publication Nos. 2010/0137143, and 2010/0282617, each of which is hereby incorporated by reference in its entirety for all purposes.

Accordingly, there is a need for further data analysis methods and systems that can efficiently process and analyze large volumes of data relating to nucleic acid sequence analysis and more particularly, to align or map nucleic acid fragments or sequences of various lengths. Further, there is a need for new data analysis methods and systems that can efficiently process data and signals indicative of electronically-detected chemical reactions, for example, nucleotide incorporation events, and transform these signals into other data and information, for example, base calls and nucleic acid sequence information and reads, which then can be aligned, for example, against a reference genome.

SUMMARY

In light of the foregoing, the present teachings provide new and improved methods and systems for nucleic acid sequence analysis that can address and analyze data reflective of electronically-detected chemical targets and/or reaction by-products associated with nucleotide incorporation events without the need for exogenous labels or dyes to characterize nucleic acid sequences of interest. In various embodiments, the present teachings describe methods and systems that can process such data and various forms thereof including nucleotide flow orders to align or map fragments of the nucleic acid(s) of interest. These methodologies also can be applied to conventional sequencing techniques and in particular, sequencing by synthesis techniques.

In various embodiments, the present teachings describe a method of aligning a putative nucleic acid sequence or fragment of a sample nucleic acid template or complement thereof against a candidate reference nucleic acid sequence. The method generally can include generating a putative nucleic acid sequence of a sample nucleic acid template based on a series of nucleotide flows to a defined space and obtaining a series of signals from the defined space, where the sample nucleic acid template is associated with the defined space. The method can include identifying, based on the putative nucleic acid sequence, a candidate reference nucleic acid sequence to which the putative nucleic acid sequence may be aligned. The method can include forming, for at least one base corresponding to the series of nucleotide flows, a matrix having two axes and a plurality of cells. Each cell can correspond to a specific row and column of the two axes, where the matrix comprises a first axis corresponding to the nucleobases of the candidate reference nucleic acid sequence and a second axis comprising a listing of the number (from 0 to n) of nucleobases in a homopolymer of the nucleobase of the nucleotide flow. The method can include calculating the value of each cell of the matrix in response to the overlap of the nucleobase of the nucleotide flow with each nucleobase of the candidate reference nucleic acid sequence using a local sequence aligning method, for example, a Smith-Waterman local sequence alignment algorithm. The method also can include weighting each value of the matrix in response to the signal corresponding to one or more of the nucleobase of the nucleotide flow. The method can include tracing back through each of the matrices for each of the nucleobases of the series of nucleotide flows to determine the goodness of fit.

In various embodiments, the goodness of fit can be against the putative nucleic acid sequence. In other embodiments, the goodness of fit can be against the sample nucleic acid template. In certain embodiments, the goodness of fit can be against both the putative nucleic acid sequence and the sample nucleic acid template. In some embodiments, the method can include identifying more than one candidate reference nucleic acid sequence and the actions of forming, calculating, weighting and tracing described above can be performed for the additional candidate reference nucleic acid sequences. In certain embodiments, the method can include calculating an alignment score for each alignment against a different candidate reference nucleic acid sequence.

In various embodiments, each of the series of signals can be representative of the incorporation of nucleobases in a sample template reflected for example as a change in hydrogen ion concentration in a defined space.

In certain embodiments, calculating the value of each cell of the matrix can include scoring an alignment. In particular embodiments, scoring an alignment can include setting a match parameter value, a non-match parameter value, and a gap parameter value. In various embodiments the local sequence aligning method can include determining the maximum of $Cell_{i-1,j-1}$+a score, $Cell_{i-1,j}$+a first gap penalty, and $Cell_{i,j-1}$+a second gap penalty.

In various embodiments, weighting can be performed by a function in response to the difference between a measured signal for a nucleobase of the series of nucleotide flows and an estimated value of that nucleobase. In some embodiments, weighting can be performed by a function in response to an approximated homopolymer number or length. In certain embodiments the function can be determined as the absolute value of the difference between the homopolymer number and the measured signal multiplied by a calculated or predetermined penalty.

In particular embodiments, a method of aligning a putative nucleic acid sequence of a sample nucleic acid template or fragment against a candidate reference nucleic acid sequence can include forming a 3-dimensional matrix having a plurality of cells, each cell corresponding to a specific row and first and second columns of the three axes, wherein the matrix can include a first axis corresponding to the nucleobases of a candidate reference nucleic acid sequence, a second axis corresponding to a listing of the number (from 0 to n) of nucleobases in a homopolymer of the nucleobase of the nucleotide flow, and a third axis corresponding to the nucleobases of a series of nucleotide flows. The method also can include finding a desired or best path through the cells of the matrix to determine the goodness of fit of the candidate reference nucleic acid sequence, where the candidate reference nucleic acid sequence is identified based on a putative nucleic acid sequence and the putative nucleic acid sequence is based on a series of nucleotide flows to a defined space and a series of signals from the defined space.

Numerous embodiments of the present teachings include a computer-useable medium having computer readable instructions stored thereon for execution by a processor to perform the various methods described herein.

The methods also can include transmitting, displaying, storing, or printing; or outputting to a user interface device, a computer readable storage medium, a local computer system or a remote computer system, information related to one or more of the alignments and the information associated with the alignments, such as the sample nucleic acid template, the signals, the defined space, the matrices, and equivalents thereof.

The present teachings also include a computer-useable medium having computer readable instructions stored thereon for execution by a processor to perform various embodiments of methods of the present teachings. It should be understood that the signals described herein generally refer to non-transitory signals, for example, an electronic signal, unless understood otherwise from the context of the discussion.

In various embodiments of systems of the present teachings for nucleic acid sequence analysis, a aligner module can be configured to practice and/or carry out various methods of the present and/or teachings as described herein and as understood by a skilled artisan.

It is to be understood that both the foregoing general description and the following detailed description are exemplary and explanatory only and are not intended to limit the scope of the present teachings.

BRIEF DESCRIPTION OF THE DRAWINGS

The present teachings described herein will be more fully understood from the following description of various illustrative embodiments, when read together with the accompanying drawings. It should be understood that the drawings described below are for illustration purposes only. The drawings are not necessarily to scale, with emphasis generally being placed on illustrating the principles of the present teachings. The drawings are not intended to limit the scope of the present teachings in any way.

FIG. 3 discloses SEQ ID NO:1.

DETAILED DESCRIPTION

Figure 1:
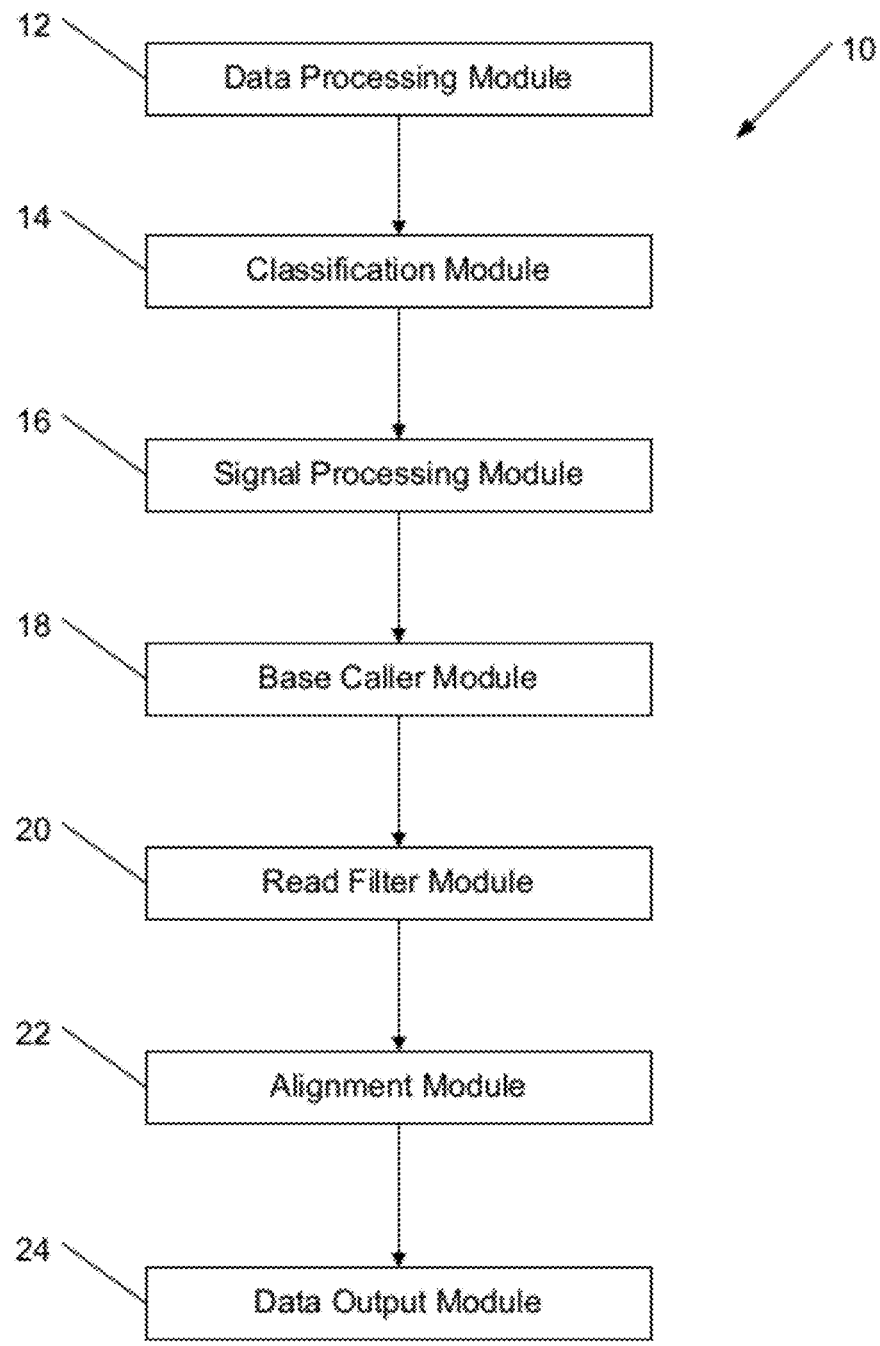
FIG. 1 is a schematic diagram depicting an exemplary system for nucleic acid sequence analysis according to the present teachings.

Nucleic acid sequence analysis can be conducted using electronic sensors that generate signals indicative of enzymatic or chemical reactions associated with nucleotide incorporation events to provide an identification of a sample nucleic acid sequence. More specifically, the present teachings provide methods and systems for the analysis of signals relating to consecutive base calls of fragments of a sample nucleic acid sequence of interest followed by the alignment of the fragments into a longer sample nucleic acid sequence. The methods can include transmitting, displaying, storing, printing, or outputting information related to one or more parameters or variables of the analysis, including equivalents thereof. The present teachings describe methods and systems that can accomplish such analyses through a variety of different processing and analysis protocols, procedures, schemes, and associated hardware.

Although the present teachings can have multiple, varied applications (including non-sequencing applications) and be used with data from various analytical instruments, apparatus and systems, the present teachings and description herein will be focused on data and signals indicative or representative of changes in hydrogen ion concentration or pH, which can be associated with incorporation of a nucleotide into a polynucleotide, for example, a nucleic acid template strand. Such data can be generated, for example, by Ion Torrent's Personal Genome Machine™ ("PGM™") or "Proton™", available from Life Technologies Corporation (Carlsbad, Calif.), which is used as an exemplary analytical sequencing instrument on which to focus the discussion herein. Consequently, it should be understood that references herein to actions, structure and apparatus specific to the PGM/Proton will apply equally to more general or generic actions, structure and apparatus, and vice versa, unless indicated to the contrary. For example, references to a well should apply equally to a defined space, a reaction space, a reaction chamber, or an area; references to a chip should apply equally to a reaction-permitting device or apparatus capable of association with an electronic sensor detection apparatus, for example, ISFET, CMOS, or other sensors; and so on. However, it also should be understood that the methods and systems of the present teachings can be useful in other applications and should not be limited by the exemplary discussion herein. For example, the present teachings may be applied to other technologies including those which utilize fluorescent markets, labels, or [ ].

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," "having," "contain," "contains," or "containing" should be generally understood as open-ended and non-limiting unless specifically stated otherwise.

As used herein, "a" or "an" may also refer to "at least one" or "one or more". Further, unless expressly stated to the contrary, "or" refers to an inclusive- or and not to an exclusive- or. For example, a condition A or B is satisfied by any one of the following: A is true (or present) and B is false (or not present), A is false (or not present) and B is true (or present), and both A and B are true (or present).

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "nucleobases" can refer to the bases of a polynucleotide sequence, such as adenine ("A"), guanine ("G"), cytosine ("C"), uracil ("U"), or thymine ("T"). As used herein, "homopolymer" can refer to a length of polynucleotide sequence in which a nucleobase is repeated, such as "AAAA".

As used herein, "nucleotide flow" can refer to a cycle or "flow" of deoxynucleoside triphosphate ("dNTP") addition from which nucleotide incorporations may result.

At various places in the present specification, substituents are disclosed in groups or in ranges. It is specifically intended that the description include each and every individual subcombination of the members of such groups and ranges. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

It should be understood that the order of steps or order for performing certain actions is immaterial so long as the present teachings remain operable. Moreover, two or more steps or actions can be conducted simultaneously.

The present teachings provide methods and apparatus for analyzing data, for example, data and signals, resulting from label-free nucleic acid (e.g., deoxyribonucleic acid ("DNA")) sequencing techniques, and in particular, hydrogen ion producing and pH-based nucleic acid sequencing techniques. Label-free nucleic acid sequencing techniques and instruments, including methods for electronic detection of pH-based nucleic acid sequences, are described in Rothberg et al., U.S. Patent Application Publication No. 2009/0026082 and other patent publications cited herein.

Briefly, in pH-based nucleic acid sequencing, a nucleotide incorporation event can be determined by measuring hydrogen ions that are generated or evolved as natural by-products of polymerase-catalyzed nucleotide extension reactions. In some embodiments, templates (e.g., fragments of a nucleic acid sequence of interest) each having a primer and polymerase operably associated localized in reaction areas such as microwells, after which repeated cycles or "flows" of deoxynucleoside triphosphate ("dNTP") addition and washing are carried out. In certain embodiments, such templates can comprise clonal populations and further may be secured to a solid support, such as a microparticle, bead, or the like (as used herein, generally, "particles"). In various embodiments, clonal populations affixed to beads or particles are loaded into reaction chambers. For example, templates can be prepared as disclosed in U.S. Patent Application Publication No. 2010/0304982 for sequencing and analysis in the manner described herein.

In one exemplary approach, a primer can be annealed to a template so that the primer's 3' end can be extended by a polymerase whenever appropriate dNTPs are available. The polymerase extends the primer by incorporating dNTPs when the next base in the template is the complement of the added dNTP. If there is one complementary base, there is expected to be a single incorporation; if two, then two incorporations are expected; if three, then three incorporations are expected; and so on. With each such incorporation, hydrogen ions are released, and collectively a population of templates releasing hydrogen ions changes the local pH of the reaction chamber.

The production of hydrogen ions is monotonically related to the number of contiguous complementary bases in the template (as well as the total number of template molecules with primer and polymerase that participate in an extension reaction). Thus, when there is a number of contiguous complementary bases of similar composition in the template, such as a homopolymer region, the number of hydrogen ions generated, and therefore the relative magnitude of the local pH change, is generally proportional to the number of contiguous complementary bases. The corresponding output signals are sometimes referred to as "1-mer", "2-mer", "3-mer" output signals, and so on.

If the next base in the template is not complementary to the added or flowed dNTP, then no incorporation occurs and no hydrogen ion is generated or released (in which case, the output signal is sometimes referred to as a "0-mer" output signal.) Between successive nucleotide additions, a wash solution typically with a predetermined pH can be used to remove residual dNTPs of the previous step in order to prevent undesired misincorporations in later cycles, such as undesirable nucleotide carryover from one flow to another. In various embodiments, one of the different types of dNTPs is added sequentially to the reaction chambers so that each reaction chamber is exposed to the four different types of dNTPs, one at a time. Each exposure to a nucleotide optionally followed by a washing step can be considered a "nucleotide flow." Consecutive nucleotide flows can be considered a "cycle." For example, a two cycle serial nucleotide flow order can be represented by: dATP, dCTP, dGTP, dTTP, dATP, dCTP, dGTP, dTTP, (or ACGTACGT) with each exposure followed by a wash step.

Thus, based on the known nucleotide flow order to a reaction chamber and the signals indicative of hydrogen ion concentration in the reaction chamber resulting from each nucleotide flow, the identity of the type, sequence and number of nucleotide(s) associated with a sample nucleic acid template present in the reaction chamber can be determined. Subsequently, where the sample nucleic acid templates include or are fragments of one or more sample nucleic acid sequences, the sample nucleic acid sequences (or at least portions thereof) can be determined by aligning appropriately the sample nucleic acid templates, reference sequences, or to other sample fragment sequences.

To measure the hydrogen ions produced by a nucleotide incorporation event in a particular reaction chamber, methods and apparatus that can carry out and monitor a plurality of multi-step reactions with electronic sensors can be used. For example, the electronic sensors can be integrated into a sensor array suitable for simultaneously sensing individual reactions taking place on or adjacent to or in sensing relationship with a surface of an array. In some embodiments, an array of defined spaces or reaction areas can be integral with or coupled to such a sensor array.

The defined spaces and/or reaction spaces provide an area or a volume where a fluid or a solid can be confined, retained and/or localized. The area or the volume can be a predetermined area or a predetermined volume, for example, a depression a micro-machined well associated with a microwell plate, microtiter plate, microplate, or a chip of semiconductor material (a "semiconductor chip"), which chip can define the reaction spaces or chambers such as wells. The area or the volume of a defined space also can be determined based on the amount of fluid or solid deposited on a substrate or in a volume otherwise defining a defined space. For example, isolated hydrophobic areas on a generally hydrophobic surface can provide defined spaces. A defined space includes a reaction chamber, such as a well or a microwell.

An array of defined spaces can take the form of a microwell array or a reaction chamber array made by conventional micro- or nanofabrication techniques, for example, as described in Rothberg et al., U.S. Patent Application Publication No. 2009/0127589; and Rothberg et al., U.K. Patent Application No. GB 24611127. In particular embodiments, each microwell or reaction chamber in an array can be in a sensing relationship, for example, electrical communication, with at least one sensor. In such an arrangement, one or more characteristics of the conditions in the microwell or reaction chamber can be detected or measured. The electronic sensors can convert changes in the presence, concentration or amounts of reaction by-products (or changes in ionic character of the reactants) into an output signal, which can be registered electronically, for example, as a change in a voltage level or a current level which, in turn, can be processed to extract information about a chemical reaction or desired association event, for example, a nucleotide incorporation event. Of course if no change occurs in the defined space, then the output signal can remain relatively constant or no signal may be generated.

The sensors of the array can comprise at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of physical property (or a change in such value), such as ion concentration. Exemplary configurations and physical characteristics of electronic sensor arrays and microwell arrays are described in U.S. Patent Application Publication Nos. 2010/0304982 and 2009/0127589; and U.K. Patent Application No. GB 24611127. In various embodiments, each of the electronic sensors of the array can generate an output signal that depends in part on the value of the voltage of a reference electrode that is in fluid communication with a microwell array. In certain embodiments, a single reference electrode configuration can be used so that each sensor generates an output signal with the same reference voltage.

The initial measurement or interrogation of a defined space, for example, a pH measurement can be represented as an electrical signal or a voltage, which also can be digitalized (e.g., a digital representation of the electrical signal or the voltage). Any of these measurements and representations can be considered data or a signal.

Accordingly, in various embodiments, the methods of the present teachings generally include generating and processing a series of signals indicative of the hydrogen ion concentration of a defined space or plurality of defined spaces such as an array of reaction wells associated with an array of sensors, where the defined space(s) comprise a sample nucleic acid template and associated enzymes and reagents used in nucleotide incorporation. The method can include processing the generated signals to identify the type, number, and/or sequence of nucleotides of the sample nucleic acid templates, thereby providing one or more reads comprising consecutive base calls associated with the sample nucleic acid templates. The method also can include aligning the reads of a plurality of sample nucleic acid templates to determine longer stretches of a sample nucleic acid sequence. The method further can include transmitting, displaying, storing, or printing; or outputting to a user interface device, a computer readable storage medium, a local computer system or a remote computer system, information related to the analysis, which information can include data and signals and results of the analysis of the data and signals. Such information can take the form of searchable and/or filterable lists of runs and reports, pictures, tables, charts, graphs, spreadsheets, correlations, sequences, and combinations thereof.

Systems of the present teachings include various hardware and components useful to carry out various embodiments of the methods of the present teachings. As shown in FIG. 1, a system 10 of the present teachings generally can include a data processing module 12, a classification module 14, a signal processing module 16, a base caller module 18, a read filter module 20, an alignment module 22, and a data output module 24. Such a system or a variation thereof, can be set-up to be accessible through a web-accessible data portal. In certain embodiments, the methods of the present teachings include the general steps associated with the modules shown in FIG. 1 such that the signals or data are processed from the data processing module to the data output module. Each of the components of the system and actions and features of methods of the present teachings will be discussed in more detail below under an appropriate heading. It should be understood that the description of embodiments the systems and associated actions can be applied equally to the methods of the present teachings, and vice versa.

Data Processing Module

A data processing module generally is configured to receive data as a series of signals, which can be reflective or indicative of a natural by-product(s) of a transforming chemical reaction. For example, for the PGM, the signals are derived from nucleotide incorporation events (e.g., incorporation of a dNTP associated with a sample nucleic acid template) by measuring hydrogen ions that are generated as natural by-products of polymerase-catalyzed nucleic acid extension reactions. More specifically, the hydrogen ion concentration (or pH) of a defined space can be measured repeatedly and at intervals timed to coincide with the nucleotide flows of different types of dNTPs to the defined space. For the PGM, the signals can represent a conversion of the pH value in each well into a voltage, which then can be converted into a digital representation of that voltage. While exemplified in the context of electronic detection of hydrogen ions released following a nucleotide incorporation event, it will be appreciated that the methods described herein can be adapted for use with other sequencing approaches such as sequencing by synthesis (SBS), and other electronic and non-electronic detection techniques, such as those using fluorescent tags or labels.

More specifically, during a PGM run, for each nucleotide flow, an acquisition file may be generated. The acquisition file may contain the signals from selected wells of a chip for the given nucleotide flow. For a chip that contains about 1.5 million wells, each nucleotide flow can result in about 1.5 million separate nucleotide sample incorporation events. Following this through to its conclusion, for a series of nucleotide flows or a series of resultant signals may be captured or saved and reflect nucleotide incorporations over time.

A read can represent consecutive base calls associated with a sequence of a nucleic acid. A read can reflect bases or base complements associated with a sample nucleic acid template, which can be associated with or present in a defined volume such as a well or associated with a defined area such as on a surface of a substrate. It should be understood that a read can include the full length sequence of the sample nucleic acid template or a portion thereof. A read can comprise a small number of base calls, such as about eight nucleotides (base calls) but can contain larger numbers of base calls as well, such as 16 or more base calls, 25 or more base calls, 50 or more base calls, 100 or more base calls, or 120 or more nucleotides or base calls. The length of a read also can be expressed as a number of base pairs (bps) for one or more sample templates.

The data processing module can perform multiple functions, including receiving or loading data, decompiling data, and offset correcting data. In various embodiments, the data processing module can receive signals into its memory, which signals can be temporarily or permanently stored. For example, the data or signals can stream off of an analytical instrument directly to the data processing module. Alternatively or in combination with direct steaming, the data processing module can access or receive the data or signals after storage or collection on a computer-readable medium such as a portable disk or hard drive. During the receiving and/or storing, the signals can be compressed and decompressed as desired.

In some embodiments, the methods can include operating in a dynamic frame rate compression mode whereby various portions of a nucleotide incorporation event or a nucleotide flow are captured at different frame rates. The variable frame rate allows biologically specific events to be captured with high resolution, while at the same time allowing the overall file size to be decreased by allowing multiple frames to be averaged where appropriate. A compression approach can use a key frame and/or delta compression technique whereby an initial value is stored, followed by the changes in that initial value, rather than storing the actual value each time. Such an approach can result in a nearly two times reduction in file size. Various embodiments of dynamic frame rate compression are described in U.S. patent application Ser. No. 13/339,846, filed Dec. 29, 2011 incorporated herein by reference.

In certain embodiments, the data processing module can perform signal offset and/or background corrections. Signals can be stored using the values output by the analytical instrument. Each defined space can have its own reference value. To compare defined space to defined space, the two defined spaces can use a common reference. The offset and/or background correction can take the average of the first few frames within each acquisition file and subtract that value from each defined space, thus allowing measurements within the defined space to have a common reference value.

In particular embodiments, the data processing module can perform pinned defined space identification. Due to the nature of the output voltages, a range of values can exist for any given sensor array. For example, applying an instrument calibration can bring the majority of defined spaces within range of the hardware's analog-to-digital converters ("ADC"), some defined spaces can fall outside that range. The output can be a distribution of values centered around the center voltage. Defined spaces or wells that reside outside a selected distribution can be considered "pinned" (functional defined spaces outside of the range of the ADC). In practice though, pinned wells or sample containment regions typically represent a small percentage or fractional percentage of the total available sample processing areas associated with the sensor array.

In various embodiments, the data processing module can flag or exclude certain defined spaces. Various flow cell configurations associated with the sensor array make tradeoffs on flow velocity profiles and sensor array coverage areas. For example, in certain sensor arrays, a percentage of the defined spaces can be covered or obscured by the flow cell components or packaging, or otherwise fluidically are inaccessible or unaddressable. Consequently, a mask can be loaded, per chip type, to mark those defined spaces as excluded so as to avoid unnecessary and/or computationally inefficient downstream processing of the sensor array and signals generated therefrom, where the information likely will be uninformative and/or unproductive.

In particular embodiments, the data processing module can receive directly acquisition files in DAT file format (e.g., acq_*.dat files), for example, streaming from an analytical instrument. In some embodiments, the data processing module can store, transmit or output the data, modified data, results and/or information in an appropriate data file.

Classification Module

Because the data can include signals from thousands to millions of individual wells or sample containment regions, reducing the amount of data to be analyzed can increase efficiency and conserve file storage space. Accordingly, sample regions of the sensor array can be classified as to whether the well generally contains useful information and should be carried forward and included in the analysis, for example, using a defined space identification module. It should be understood that while certain data can be screened or otherwise modified, in practice most data usually is saved so that various screening and manipulating of the data can be started anew, with different analysis protocol and parameters, if desired. Accordingly, not all embodiments of methods of the present teachings necessarily include each of the modules and/or steps described herein.

In various embodiments, the classification module or classifying can include processing an array of wells in smaller regions rather than the entire array as one group. For example, a chip which contains an array of about 1.5 million wells can be segmented into 50×50 well regions, resulting in about 625 total regions. Such segregation can process many smaller regions in parallel and takes advantage of, for example, parallel computing techniques, such as multi-core and/or multi-process compute nodes that have such parallel computational capabilities. Regions in the chip that can contain fluidically similar wells can be processed similarly or together as smaller regions tend to be relatively homogeneous and allow comparison of wells to each other within a region.

In addition to reduction and segregation of the amount of data to be analyzed, the classification module also can include identifying and parsing sample nucleic acid templates or fragments based on their origin, for example, with a sample nucleic acid template identification module. That is, when using test nucleic acid fragments as a control and/or when pooling and sequencing fragmented samples of nucleic acids from different origin ("multiplexing"), the test fragment and nucleic acid fragment sequences can be labeled or tagged prior to the sequencing process so that the resulting data can be appropriately analyzed. To this end, size-based and fluorescent tags can be used. Additionally, the methods and systems of the present teachings can use sequencing keys, e.g., a known nucleic acid sequence associated with a sample fragment, to identify and classify the resulting data and nucleic acid sequencing information.

Further, when a nucleic acid sequencing method uses sequencing keys as identifiers of the nucleic acid fragments to which the sequencing keys are associated, a classification module can include a sequencing keys separation module. That is, the sequencing keys should be designed to be readily identified and separated such that the identification of a read based on its sequencing key can be made with a certain level of confidence, for example, early in the data analysis process and/or based on minimal amounts of data. Various embodiments of using sequencing keys are described in U.S. patent application Ser. No. 13/340,490, filed Dec. 29, 2011 incorporated herein by reference.

Figure 2:
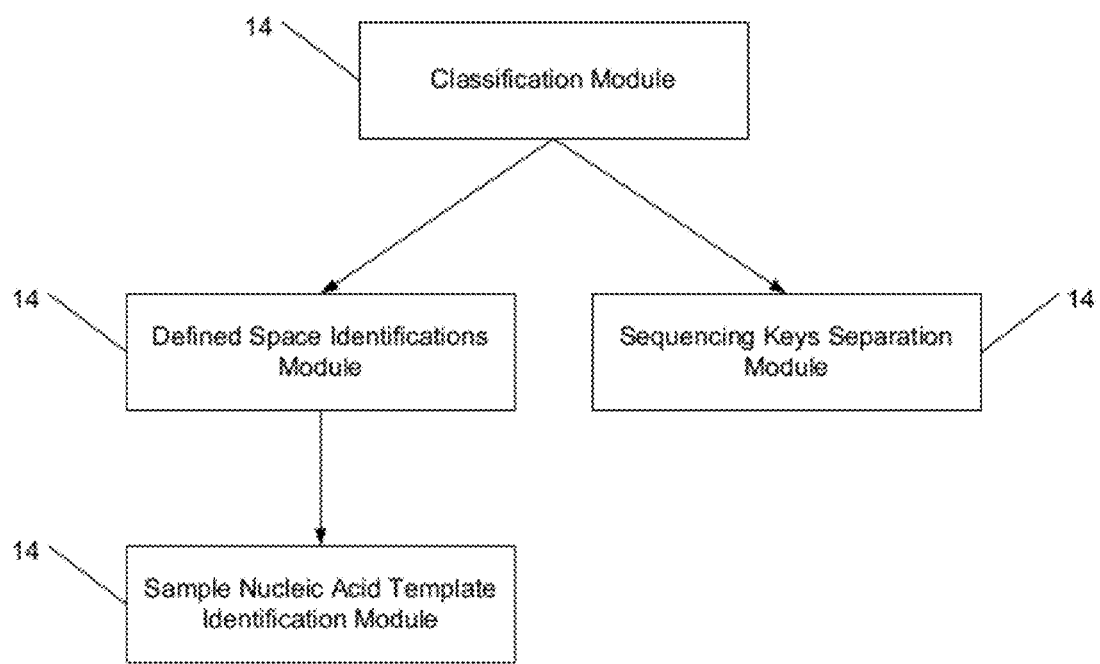
FIG. 2 is a schematic diagram depicting an exemplary system for classification according to the present teaching.

In sum, as shown in FIG. 2, a classification module 14 can include a defined space identification module 142 and a sample nucleic acid template identification module 144, both of which can process data from signals from defined spaces to evaluate, identify, flag, and/or exclude unuseful data while useful data can be processed further. The classification module 14 also can include a sequencing keys separation module 146, which can evaluate and determine the degree of separation or the "orthogonality" of a pair of sequencing keys or bar codes.

However, first understanding the source of the contents of the wells can be helpful. In some embodiments, when an array of wells is prepared for analysis, fragments of a nucleic acid sequence of interest (e.g., sample nucleic acid templates) can be associated with a surface, for example, of a particle. Each sample nucleic acid template can be associated with a surface via covalent bonding or a specific binding or coupling reaction. A sample nucleic acid template can be derived from, for example, a shot-gun fragmented DNA or amplicon library (which are examples of library fragments), a sample emulsion PCR process creating clonally-amplified sample nucleic acid templates on particles such as IonSphere™ particles.

A sequencing key can be associated with, such as added to the 5' end, the sample nucleic acid template. In such a position, the sequencing key can be near the beginning of a read to permit early identification and classification of the sample nucleic acid template, for example, as a test or a library fragment or where no identification can be made, as an ambiguous read or particle. Early classification can assist in reducing the analysis time, for example, by determining whether useful information is present and whether to exclude particular data from further processing and analysis.

In addition to unknown nucleic acid fragments of interest and sequencing keys, test nucleic acid sequence fragments ("test fragments") having a known nucleic acid sequence can be associated with particles. Test fragments often can be used as a reference and/or for quality control. Test fragments also can be considered examples of a sample nucleic acid templates.

Figure 3:
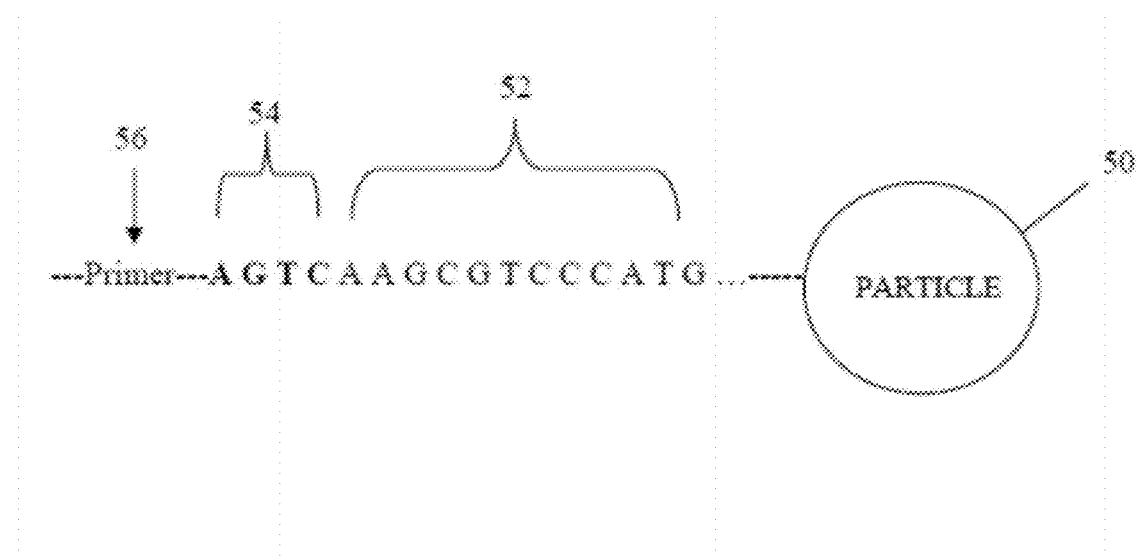
FIG. 3 is a schematic diagram depicting an exemplary structure where a sample nucleic acid template, a sequencing key, and a primer sequence are associated with a particle in accordance with the present teachings.

To maintain the integrity of sample data from a well and its output, it can be desirable to have only one fragment or nucleic acid sequence (including its clones or copies) associated with a single particle. Further, each well can be configured to contain a single particle (and thus, a single copy or population of copies of a single sample nucleic acid template can be associated with the well). The particles having library fragments and test fragments associated therewith then can be introduced randomly into an array of wells on a chip. FIG. 3 shows an exemplary particle 50 associated with a sample nucleic acid template (non-bold nucleotides) 52, a sequencing key (bold nucleotides A G T C), and primer 56.

Moreover, although a well can contain a particle (e.g., not be an "empty well" but a "particle-containing well"), the information obtained from the well can be unreliable due to no or low signal strength, ambiguous identification of the sample nucleic acid template, and/or a particle with more than one type of sample nucleic acid template or fragment (e.g., polyclonal). Consequently, a classification module generally is configured to determine the contents of each well.

Figure 4:
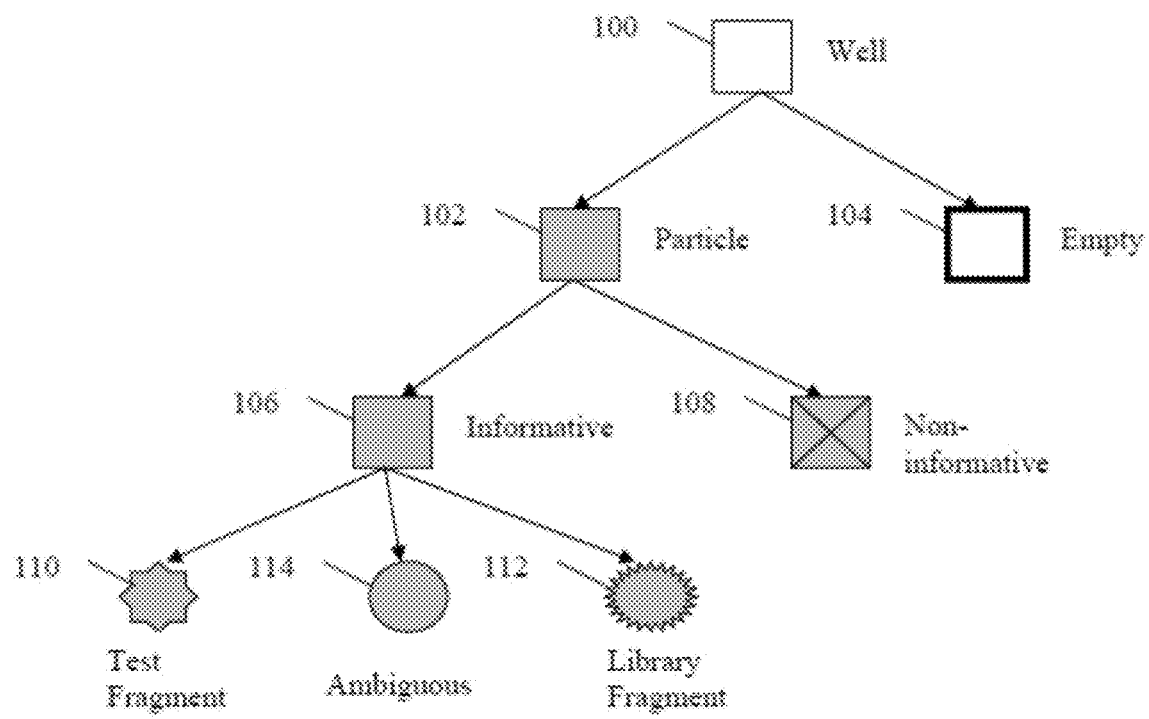
FIG. 4 is a schematic diagram depicting an exemplary process of classifying a well according to the present teachings.

FIG. 4 schematically shows an overview of an exemplary classification of a well of a chip using signals from the well, for example, as can be accomplished with a defined space identification module and a sample nucleic acid template identification module. Generally, a well 100 first can be determined to be a particle-containing well 102 or to be an empty well 104 (one without a particle). The particle-containing well 102 can be divided into a useful well 106 (one that provides useful information) and a non-informative well 108 (one that does not provide useful information). Finally, using the sample nucleic acid template identification module, the useful well 106 can be divided into a well containing test fragments 110, a well containing library fragments 112, or a well for which a determination cannot be made (ambiguous wells) 114.

Although data typically is generated and measured and/or recorded from each well for each nucleotide flow, not all of the wells contain particles nor those wells with particles have nucleic acid sequences of interest or provide useful and reliable information. Accordingly, as a first cut, data analysis can be narrowed to signals from wells containing a particle. If a well does not contain a particle, it generally will not provide useful information relating to a nucleotide incorporation event. Nevertheless, a well without a particle can be useful for certain background readings and corrections and other information relating to fluid flow and nucleotide flow(s) to the wells.

In certain embodiments, a known pH buffer at a different pH than the wash buffer can be distributed across the chip. The chip sensors can detect the pH change over time. Due to the diffusion rates on the wells and the pH concentration, the change over time can be measured. Empty wells will generally have a different rate of pH change or equilibration than particle-containing wells due to the change in diffusion properties of those wells containing a particle. In particular embodiments, for a given well, in order to determine whether the well contains a particle or is empty, the average of neighbor wells can be compared to the well in question. If the diffusion rate in the well in question is slower than the average rate of surrounding neighbors, then this well can be considered to contain a particle. Otherwise the well can be identified as empty. Additional procedures to establish a baseline pH change over time can include, for example, fitting the signal to exponentials or other models of the expected background signal.

At a next level, a particle-containing well may not produce a sufficient signal or reading to be reliable (e.g., be a "dud particle"). For example, in particular embodiments, if a well does not produce a sufficient signal over the first few to several key nucleotides (as described below), such a well can be excluded from further analysis. In general, signals tend to be strongest and/or most consistent in the early nucleotide flows of a sequence analysis. In addition, a sample nucleic acid template or fragment to be sequenced can have appended to it a known nucleic acid sequence or sequencing key, which can be used to identify the origin of the sample nucleic acid template or fragment. A key nucleotide can be a nucleotide that is present in such a sequencing key. By evaluating the information obtained during the initial nucleotide flows, wells which do not conform to an expected signal strength or sequence identification can be flagged or excluded from further analysis. Such approaches as described herein can result in efficient data analysis because only wells with potentially useful information are analyzed.

Sequencing Keys

In some embodiments, for particle-containing wells with a sufficiently strong sequence and/or accurate signal (e.g., as determined by evaluating key nucleotide data), a sample nucleic acid template identification module within the classification module can determine if that particle is associated with fragments of a nucleic acid sequence from the library of interest (a "library particle"); with a test nucleic acid sequence fragment (a "test fragment particle"); or whether a meaningful distinction between a library and test fragment cannot be made (an "ambiguous particle").

In various embodiments, the identification of a particle as being associated with a library fragment or a test fragment can be accomplished using sequencing keys and/or barcodes. In various embodiments, the sequencing keys can be viewed as a unique identifier, such as a bar code, of the origin of the sample nucleic acid template or population of nucleic acid fragments to permit appropriate sorting and/or association of nucleic acid sequences randomly dispersed in an array. Certain approaches can use multiple sequencing keys. For example, where the nucleic acid sequences (fragments) in the wells have three or more different origins (e.g., two original nucleic acid sequence populations of interest and a test fragment sequence), three or more sequencing keys or barcodes can be used to differentiate the origin of each fragment so as to allow later grouping of and/or sorting of the fragments based on the sequencing key or barcode appended thereto.

In an exemplary embodiment where two sequencing keys are used, one sequencing key can be a "library sequencing key," for example, a known artificial nucleic acid sequence identified or associated with a fragment of a nucleic acid sequence from a library. The library sequencing key can be associated with or be part of an adapter sequence or have another association with the particles which include fragments from the library of a nucleic acid sequence of interest. The other sequencing key can be a "test fragment sequencing key," for example, a known artificial nucleic acid sequence identified or associated with a known fragment of a nucleic acid used as a control or reference. If the library sequencing key and the test fragment sequencing key are distinct identifiers of each key, then a comparison of a read of unknown origin against each of the library sequencing key and the test fragment sequencing key should produce a match or a comparison of sufficient confidence. If such identification cannot be made, then the information from that well can be flagged, discarded, or ignored as being an ambiguous well.

Depending on the format of the signals at the time of classification, a comparison of a sequencing key of a read to the reference sequencing key(s) can be done in base-space format (e.g., using nucleotide designations such as A, C, G, and T). However, if the classification is done at an earlier stage of data processing, the read may be not yet in base-space format but can be in flow-space format (e.g., a series of zeros and ones representing a nucleotide incorporation event (a one, "1") or a non-incorporation event (a zero, "0") for that particular nucleotide flow). (It should be understood that zeros and ones are convenient representations of a non-incorporation event and a nucleotide incorporation event; however, any other symbol or designation could be used alternatively to represent and/or identify these events and non-events). In certain embodiments, a homopolymer region can be represented by a whole number greater than one rather than the respective number of one's in series. In flow-space format, the nucleotide flow order determines the flow-space format or flow order vector.

For example, for a base-space sequence of "AT," and a nucleotide flow order of "TACG," the flow-space vector would be "0100X." That is, the first nucleotide flow of "T" does not match the first nucleotide of the template, such as, "A," and would result in a non-incorporation event ("0"). The second nucleotide flow of "A" is a match and would result in a nucleotide incorporation event ("1"). The third nucleotide flow of "C" and the fourth nucleotide flow of "G" do not match the second nucleotide of the template, such as, "T," and hence two consecutive zeros ("0, 0") are added to the flow-space vector. The fifth nucleotide flow of "T" is a match and would result in a nucleotide incorporation event. However, because additional "T's" could present in the extended sample nucleic acid template (e.g., the extended nucleic acid template could be "ATTTG"), additional nucleotide incorporation events could occur during this fifth nucleotide flow. Consequently, an "X" is placed in the flow-space vector indicating a nucleotide incorporation event that may have been truncated.

Table 1 shows exemplary library and test fragment sequencing keys in both base-space format and in flow-space format for a nucleotide flow order of TACG.

TABLE 1

| | Base-space format | Flow-space format* |
|---|---|---|
| Library Sequencing Key | TCAG | 1010010X |
| Test Fragment Sequencing Key | ATCG | 0100101X |

*based on nucleotide flow order TACG

Because the nucleotide flow order vector can be tested against each sequencing key, the number of nucleotide flows required to sequence each sequencing key can be determined. In particular embodiments, the lower number of nucleotide flows needed to sequence one of the sequencing keys can be used for the comparison as that number of nucleotide flows should provide sufficient information for separation.

Design of Sequencing Keys

In embodiments where sequencing keys are used to identify or separate nucleic acids of different origin, the sequencing keys should be sufficiently distinguishable so that the identification can be made with confidence. In some embodiments, the sequencing keys can be designed and compared for their orthogonality (or distinctiveness). For example, in various embodiments, each different nucleotide, such as A, C, G, and T, of the sequencing keys can be considered to be orthogonal if selected conditions or rules are satisfied for a nucleotide pair in flow-space (e.g., considering G in the first sequencing key and G in the second sequencing key).

Exemplary first condition: both a non-incorporation event ("0-mer") and a nucleotide incorporation event ("1-mer") are present in each sequencing key for the nucleotide.

Exemplary second condition: for the first occurrence of the nucleotide in the first flow-space sequencing key, a nucleotide incorporation event (1-mer) occurs while during that nucleotide flow, a non-incorporation event (0-mer) is present for the second sequencing key. In addition, the reverse is tested. That is, for the first occurrence of the nucleotide in the second flow-space sequencing key, a nucleotide incorporation event (1-mer) occurs while during that nucleotide flow, a non-incorporation event (0-mer) is present for the first sequencing key.

If these conditions or conditions are satisfied, the nucleotide pair can be considered to be orthogonal in flow-space for the two sequencing keys. A separator event occurs when the nucleotide pairs are orthogonal. An increase in the number of separator events for two sequencing keys means in an increased separation of the two sequencing keys, which increased separation can result in increased confidence in the accuracy of the identification of the origin of the read of the sample nucleic acid template.

Sequencing keys of the present teachings based on flow-space format vectors can permit the identification and classification of a sample nucleic acid template using less nucleotides than typically can be required for state-of-the-art methods where comparisons usually are done in base-space format. That is, because sequencing keys can be designed using nucleotide flow cycles and a particular nucleotide flow order to create orthogonality between or among the sequencing keys, a smaller number of nucleotides can be required to provide a distinguishable difference as to the origin of the sequence template.

The following examples of sequencing key design and evaluation of orthogonality are provided to illustrate further and to facilitate the understanding of the present teachings and are not in any way intended to limit the invention.

Example 1

To evaluate the separation of the library key sequencing key and the test fragment sequencing key in Table 1, the orthogonality of each nucleotide is tested according to the above two described conditions.

First, the flow-space format vector of the library sequencing key (top line below) is aligned with the flow-space format vector of the test fragment sequencing key (bottom line below). In this depiction, each row represents a sequencing key and each column represents a single nucleotide flow.

| 1 | 0 | 1 | 0 | 0 | 1 | 0 |
|---|---|---|---|---|---|---|
| 0 | 1 | 0 | 0 | 1 | 0 | 1 |

In addition, the "X" is not included for each sequencing key as it is an unknown.

Next, to evaluate the T nucleotide, the T nucleotide flows are identified, which in this example, correspond to the first and fifth nucleotide flows (for convenience, the numbers in the first and fifth columns are bolded and underlined below).

| _1_ | 0 | 1 | 0 | _0_ | 1 | 0 |
|---|---|---|---|---|---|---|
| _0_ | 1 | 0 | 0 | _1_ | 0 | 1 |

As can be seen in the above highlighted depiction, across each row (again, each row representing a sequencing key), a nucleotide incorporation event (bold, underlined "1") and a non-incorporation event (bold, underlined "0") occur for each sequencing key, thereby satisfying the first condition.

For the second condition, for each of the first and fifth columns (again, each column representing a single nucleotide flow), a nucleotide incorporation event (bold, underlined "1") occurs for one sequencing key while during that same nucleotide flow (same column), a non-incorporation event (bold, underlined "0") occurs for the other sequencing key. Consequently, because both conditions are satisfied, these two sequencing keys can be considered orthogonal for the T nucleotide.

To evaluate the A nucleotide, the A nucleotide flows are identified, which in this example, correspond to the second and sixth nucleotide flows (for convenience, the numbers in the second and sixth columns are bolded and underlined below).

| 1 | _0_ | 1 | 0 | 0 | _1_ | 0 |
|---|---|---|---|---|---|---|
| 0 | _1_ | 0 | 0 | 1 | _0_ | 1 |

As can be seen in the above highlighted depiction, across each row, a nucleotide incorporation event (bold, underlined "1") and a non-incorporation event (bold, underlined "0") occur for each sequencing key, thereby satisfying the first condition.

For the second condition, for each of the second and sixth columns, a nucleotide incorporation event (bold, underlined "1") occurs for one sequencing key while during that same nucleotide flow, a non-incorporation event (bold, underlined "1") occurs for the other sequencing key. Consequently, because both conditions are satisfied, these two sequencing keys can be considered orthogonal for the A nucleotide.

To evaluate the C nucleotide, the C nucleotide flows are identified, which in this example, correspond to the third and seventh nucleotide flows (for convenience, the numbers in the third and seventh columns are bolded and underlined below).

| 1 | 0 | _1_ | 0 | 0 | 1 | _0_ |
|---|---|---|---|---|---|---|
| 0 | 1 | _0_ | 0 | 1 | 0 | _1_ |

As can be seen in the above highlighted depiction, across each row, a nucleotide incorporation event (bold, underlined "1") and a non-incorporation event (bold, underlined "0") occur for each sequencing key, thereby satisfying the first condition.

For the second condition, for each of the third and seventh columns, a nucleotide incorporation event (bold, underlined "1") occurs for one sequencing key while during that same nucleotide flow, a non-incorporation event (bold, underlined "0") occurs for the other sequencing key. Consequently, because both conditions are satisfied, these two sequencing keys can be considered orthogonal for the C nucleotide.

To evaluate the G nucleotide, the G nucleotide flows are identified, which in this example, corresponds only to the fourth nucleotide flow (for convenience, the numbers in the fourth column are bolded and underlined below).

| 1 | 0 | 1 | 0 | 0 | 1 | 0 |
|---|---|---|---|---|---|---|
| 0 | 1 | 0 | 0 | 1 | 0 | 1 |

Here, the first condition is not satisfied because a non-incorporation event (bold, underlined "0") occurs for both sequencing keys for the first G nucleotide flow. Accordingly, these two sequencing keys can be considered not orthogonal for the G nucleotide as a separation event does not occur.

In sum, the library sequencing key and the test fragment sequencing key in Table 1 can be considered orthogonal for three of the four nucleotides.

Example 2

In this example, an alternate library sequencing key is evaluated against the test fragment sequencing key of Example 1. For these two sequencing keys, the orthogonality of each nucleotide is tested according to the above two described conditions.

The base-space format of the alternate library key is CTAG. For the nucleotide flow order of TACG, the corresponding flow-space format vector is 00101101X.

Here, note that an additional nucleotide flow is needed to sequence the alternating library sequencing key (top row) than the test fragment sequencing key (bottom row).

| 0 | 0 | 1 | 0 | 1 | 1 | 0 | 1 | X |
|---|---|---|---|---|---|---|---|---|
| 0 | 1 | 0 | 0 | 1 | 0 | 1 | X |   |

Accordingly, the number of nucleotide flows that can be used to evaluate the separation or orthogonality of these two sequencing keys can be based on the lowest number of nucleotide flows needed to sequence one of the sequencing keys. In this example, the alternate library sequencing key can be sequenced in nine nucleotide flows whereas the test fragment sequencing key can be sequenced in eight nucleotide flows. Because the last base call, designated "X," is unknown in each sequencing key because that position could represent the beginning of a homopolymer, the number of nucleotide flows that can be used for the alternate library and the test fragment sequencing keys is eight and seven, respectively. Thus, the lowest number of known nucleotide flows between the two sequencing keys is seven. Consequently, seven nucleotide flows can be used to evaluate the number of separation events between the two sequencing keys.

Accordingly, similar to Example 1, the flow-space format vector of the first seven nucleotide flows of the alternate library sequencing key (top line below) first is aligned with the flow-space format vector of the first seven nucleotide flows of the test fragment sequencing key (bottom line below) As in Example 1, each row represents a sequencing key and each column represents a single nucleotide flow.

| 0 | 0 | 1 | 0 | 1 | 1 | 0 |
|---|---|---|---|---|---|---|
| 0 | 1 | 0 | 0 | 1 | 0 | 1 |

To evaluate the T nucleotide, the T nucleotide flows are identified, which in this example, corresponds to the first and the fifth nucleotide flows (for convenience, the numbers in the first and the fifth columns are bolded below).

| 0 | 0 | 1 | 0 | 1 | 1 | 0 |
|---|---|---|---|---|---|---|
| 0 | 1 | 0 | 0 | 1 | 0 | 1 |

Here, the first condition is not satisfied because a non-incorporation event (bold "0") occurs for both sequencing keys for the first T nucleotide flow as well as a nucleotide incorporation event (bold "1") occurs for both sequencing keys for the second T nucleotide flow. Accordingly, these two sequencing keys can be considered not orthogonal for the T nucleotide as a separation event does not occur.

To evaluate the A nucleotide, the A nucleotide flows are identified, which in this example, correspond to the second and sixth nucleotide flows (for convenience, the numbers in the second and sixth columns are bolded below).

| 0 | 0 | 1 | 0 | 1 | 1 | 0 |
|---|---|---|---|---|---|---|
| 0 | 1 | 0 | 0 | 1 | 0 | 1 |

As can be seen in the above highlighted depiction, across each row, a nucleotide incorporation event (bold "1") and a non-incorporation event (bold "0") occur for each sequencing key, thereby satisfying the first condition.

For the second condition, for each of the second and sixth columns, a nucleotide incorporation event (bold "1") occurs for one sequencing key while during that same nucleotide flow, a non-incorporation event (bold "0") occurs for the other sequencing key. Consequently, because both conditions are satisfied, these two sequencing keys can be considered orthogonal for the A nucleotide.

To evaluate the C nucleotide, the C nucleotide flows are identified, which in this example, correspond to the third and seventh nucleotide flows (for convenience, the numbers in the third and seventh columns are bolded below).

| 0 | 0 | 1 | 0 | 1 | 1 | 0 |
|---|---|---|---|---|---|---|
| 0 | 1 | 0 | 0 | 1 | 0 | 1 |

As can be seen in the above highlighted depiction, across each row, a nucleotide incorporation event (bold "1") and a non-incorporation event (bold "0") occur for each sequencing key, thereby satisfying the first condition.

For the second condition, for each of the third and seventh columns, a nucleotide incorporation event (bold "1") occurs for one sequencing key while during that same nucleotide flow, a non-incorporation event (bold "0") occurs for the other sequencing key. Consequently, because both conditions are satisfied, these two sequencing keys can be considered orthogonal for the C nucleotide.

To evaluate the G nucleotide, the G nucleotide flows are identified, which in this example, corresponds only to the fourth nucleotide flow (for convenience, the numbers in the fourth column are bolded below).

| 0 | 0 | 1 | 0 | 1 | 1 | 0 |
|---|---|---|---|---|---|---|
| 0 | 1 | 0 | 0 | 1 | 0 | 1 |

Here, the first condition is not satisfied because a non-incorporation event (bold "0") occurs for both sequencing keys for the first G nucleotide flow. Accordingly, these two sequencing keys can be considered not orthogonal for the G nucleotide as a separation event does not occur.

In sum, the alternate library sequencing key and the test fragment sequencing key can be considered orthogonal for two of the four nucleotides, which separation is not as large as the library sequencing key and the test fragment sequencing key in Example 1.

It should be understood that in some embodiments, the nucleotide flow order can be altered. The only change will be the flow-space format vector to accommodate the alternate nucleotide flow order. Therefore, for any nucleotide flow order, flow-space format vectors can be created from the base call sequences (base-space format) to compare the orthogonality of the nucleotides as described and illustrated herein.

In particular embodiments, the classification module can receive directly a data file. The classification module can store transmit, or output classification information in a MASK file format (e.g., bfmask.bin), which can contain bit flags for each well, indicating the contents of each well.

Signal Processing Module

A signal processing module generally is configured to analyze signal information from a defined space and an associated sample nucleic acid template being sequenced. The signal processing module can output an incorporation signal. The signal processing module can use information and data resulting from the classification module and methods described therein, but also can use data or signals.

Several potential sources of noise can affect output signals from sensors when a large number (e.g., tens or hundreds of thousands or millions) of electrochemical reactions are carried out over an array of defined spaces. The data and signals received by the signal processing module can include background information that can be excluded in analyzing the initial signal and generating an incorporation signal.

In some embodiments, the signal processing module can focus only on defined spaces containing particles and/or those defined spaces producing a sufficiently strong signal to indicate a nucleotide incorporation event (e.g., in FIG. 1, useful wells 106). An incorporation signal indicates a nucleotide incorporation event because of the hydrogen ion concentration or pH of a defined space during a particular nucleotide flow. However, during a nucleotide incorporation event, a measured signal can have additional components, referred to as background or noise. The background or noise portion of the signal can be present during each flow and can vary over time, across an array of wells, and during an acquisition. For example, the changing pH above a series of wells can introduce a background measurement variance. Accordingly, a measured background signal can be filtered based on the well and particle properties.

In certain embodiments, the signal processing module can create an incorporation fitting model. In some embodiments, the incorporation fitting model has two parts. The first part can derive the background signal that would have been measured in a given defined space had no nucleotide incorporation event occurred. The second part can involve subtracting (or fitting) the background signal from the signal and then examining and analyzing (or fitting to) the signal that remains. The result of the incorporation fitting model can be an estimate of incorporation during each nucleotide flow for each well.

In particular embodiments, a signal processing module can receive data acquired from the sequencing reactions. The signal processing module can store, transmit and/or output incorporation signals and related information and data in specified file format. The signal processing module can further output an incorporation signal per defined space, per flow.

Base Caller Module

A base caller module generally is configured to transform an incorporation signal into a base call and compile consecutive base calls associated with a sample nucleic acid template into a read. A base call refers to a particular nucleotide, for example, dATP ("A"), dCTP ("C"), dGTP ("G"), or dTTP ("T"). The base caller module can perform one or more signal normalizations, signal phase and signal droop (e.g., enzyme efficiency loss) estimations, signal corrections, and identify or estimate base calls for each flow of each defined space. The base caller module can share, transmit or output non-incorporation events as well as incorporation events.

In some embodiments, a read can be normalized. Normalization initially can use the data and signals from the signal processing module. Using known expected 1-mer events (e.g., identified with the sequencing keys), a 1-mer average signal initially can be established. As the base caller module processes each defined space, additional base calls can be accurately determined and additional measurements then can be used to re-normalize the signals. The re-normalization process can gain a higher confidence (e.g., a higher signal-to-noise ratio) of the signal from each defined space.

In certain embodiments, observed signal droop can be attributed to DNA polymerase loss that can occur during a sequencing run. Such DNA polymerase loss usually is experienced only during nucleotide incorporation events, with values typically in the range of about 0.1% to about 0.2% over the course of a run. By averaging groups of reads in a region together and/or averaging their signals after normalization, an exponential can be fit to the resulting curve, from which the rate of signal loss over time can be extracted. Consequently, an estimate of the DNA polymerase loss during nucleotide incorporation events can be determined.

In particular embodiments, after the signal droop has been established, the signal droop can be used in a signal phase model as a constant for a read. Signal estimates can vary across an array of defined spaces, but signal droop estimates often can be assumed to be fixed for each processed region. The signal phase model then can fit the carry-forward and incomplete extension parameters for a read, over a limited number of and excluding certain nucleotide flows. The output from this fit can be an estimate of the carry-forward and incomplete extension for each defined space. The values can be averaged over small regions to reduce errors and noise in the fit. The output carry-forward and incomplete extension values can be used as inputs to other parts of the base caller module, for example, a solver function.

In various embodiments, a solver function of the base caller module can apply the phase and droop estimates to the normalized signals and make predictions of the likely signal measurements for each nucleotide flow for probable nucleotide incorporation events. The solver function can compare the actual measured value to a list of predicted values. The best fit prediction at each nucleotide flow then can be used as the base call for that flow. For example, a 0-mer, 1-mer, 2-mer, 3-mer, 4-mer, and higher order nucleotide incorporations can be predicted at each nucleotide flow. The solver function can continue such processing over the entire read. At the end of one pass, a good estimate of all base calls for that read can be made. The solver function then can iterate over the read again, applying the same phase and droop estimates at each nucleotide flow, to refine the base calls. Thus, knowledge of future bases in later nucleotide flows can be included in the model to more accurately account for carry-forward or incomplete extension effects.

In particular embodiments, a base caller module can receive data in specified file format and can store, transmit or output reads and related information in a standard flowgram format (for example, "SFF").

Read Filter Module

A read filter module generally is configured to generate quality metrics for each base call of a read and for each read of a set of reads to facilitate filtering out of low quality or uninformative reads and base calls. The identification and removal of low quality or uncertain base calls and reads can improve the efficiency and accuracy of the analysis and results. In particular, low quality base calls can be removed from the output data by filtering out entire reads and/or trimming low quality 3' ends of reads using a variety of filters and protocols. For example, the quality of a read can be improved by trimming an adapter sequence at the end of the read. These operations typically are applied as post-processing operations after the initial base calls have been estimated.

Quality Score Determination

Overall in some embodiments, a per base quality score can be assigned to each base call of a read, and the per base quality score can be written to a file along with the read itself. A per base quality score can be assigned by calculating quality metrics for the base call(s) and/or the read. The quality metrics can be analyzed individually or in combination by comparison to a pre-defined quality look-up table (a phred-like table) established through prior system training. The quality metrics can include estimates of accuracy of the current base call, the nucleotide flow, and earlier or later base calls and/or nucleotide flows for each read.

More specifically, a quality score module generally is configured to include a phred-like per base quality look-up table and a training system to generate the quality look-up table. Phred quality scores were first created by the program Phred to aid in sequencing nucleic acid (DNA) in the Human Genome Project. Phred quality scores can characterize the quality of a DNA sequence. In the present teachings, based on nucleotide flow values for each base, several quality predictors can be calculated for each base call of a read. These quality predictors can be used as part of an index to look-up an appropriate quality score for the base call in the phred-like quality look-up table.

In some embodiments, a quality look-up table can be generated by selecting a representative data set to use as a training set. The training set can use a variety of quality predictors to characterize the quality of a base call. In an exemplary embodiment, multiple quality predictors are used to capture what are believed to be the majority of features that can correlate with an indicated quality. The quality predictors can include, but are not limited to, base position, local noise, read noise, multiple incorporations, phase error, and environment noise.

The base position quality predictor can be the base position in the read from the start of the nucleic acid sequence.

The local noise quality predictor can be the noise in an immediate neighborhood of a given base. The immediate neighborhood can be varied depending on the particulars of the application and run. For example, the local noise quality predictor can be defined to be within plus or minus ($\pm$) one base of the given base. However, other definitions of an immediate neighborhood can be used in the analysis, for example, within $\pm 2$ bases of the given base.

The read noise quality predictor can be a peak-normalized expression of the mean and the standard deviation of all 0-mers and 1-mers of a read.

In the case of multiple incorporations of the same nucleotide in one nucleotide flow (a homopolymer region), the multiple incorporations quality predictor can assign to the last base in the homopolymer region a value equivalent to the total number of incorporations during that particular nucleotide flow while all other bases in the homopolymer region can be assigned a value of 1.

The phase error quality predictor can be the number of incorporations of the same nucleotide in the previous nucleotide flow.

The environment noise quality predictor can be the noise in a larger neighborhood of a given base. As with the local noise quality predictor, the area of the larger neighborhood can vary depending on the application and run. For example, the environmental noise quality predictor can be in a larger neighborhood which is defined to be within $\pm 10$ bases of the given base. However, the larger neighborhood can be defined to be within $\pm 5$ bases, $\pm 6$ bases, $\pm 7$ bases, $\pm 8$ bases, $\pm 9$ bases, $\pm 11$ bases, $\pm 12$ bases, or more.

As already mentioned, the quality predictors can be calculated from the nucleotide flow values for each base. Also using aligned reads, the quality score module can establish the various quality predictors, along with whether or not a base was called correctly to create a vector. This vector can be used as the input into a training system. In various embodiments, the quality predictors can be binned, and an extensive list of all combinations with their empirical quality score can be recorded. An algorithm can be used to summarize quality predictor values that correspond to the same quality and to select a representative subset of these combinations.

The output of the training and selection algorithm can be a (phred-like) quality look-up table in which each quality predictor can be part of an index in the table. Consequently, the established quality look-up table can be used to look up the phred-like per base quality score for a particular base call.

In certain embodiments, after a quality look-up table is generated, the quality look-up table can be used to assign a per base quality score independent of alignment. For example, the six quality predictors can be calculated for each base of a sample nucleic acid sequence template. The corresponding per base quality score can be determined by locating, in the quality look-up table, the first line for which all six calculated quality predictors are less than or equal to the quality predictor values in the quality look-up table. The quality score then can be read from the same line.

Filtering Reads

Overall in various embodiments, the read filtering module or filtering of reads can include calculating an overall quality metric representing the base caller module's ability to correct accurately and base call the signal measurements. Low quality reads can be mixed reads, poor signal quality reads, or very low copy-count reads that produce low quality nucleic acid information and sequences such that they do not fit the expected incorporation model. Reads identified as low quality typically are excluded and not written to the SFF or FASTQ file.

Various types of read filtering can occur. For example, read filtering can include targeted removal of reads that are derived from wells with non-clonal nucleic acid template populations and/or targeted removal of reads that are generally a poor fit to the base calling model's expectations for high quality data, whether because of low or poor signal quality from the well or a low copy count of sample nucleic acid templates.

More specifically, identified non-clonal nucleic acid template-containing particles or wells typically are filtered from the data as they contain a mixture of different nucleic acid templates. That is, a mixed nucleic acid template read can result from nucleic acid templates that are amplified on a single particle but are derived from multiple, different input nucleic acid templates. A mixed nucleic acid template read can occur because of the presence of two or more distinct nucleic acid fragments in the vesicle at the start of the emulsion PCR stage, or because of the collapsing together of different emulsion vesicles.

Regardless of their origin, mixed nucleic acid template reads usually can be identified by searching for reads in which an unusually large proportion of nucleotide flows are estimated to result in a nucleotide incorporation event. For example, when no mixed nucleic acid template reads exist, each particle will have a single sample nucleic acid template species amplified onto it. Based on a four-nucleobase flow cycle and uniform and random nucleotide content in the sample nucleic acid sequence template, sequencing of such a sample nucleic acid template is expected to result in approximately one-half (50%) of the nucleotide flows having a positive nucleotide incorporation event. In contrast, when a particle contains multiple different sample nucleic acid templates, or mixed nucleic acid template reads, the number of nucleotide flows in which a positive nucleotide incorporation event signal can be expected to increase substantially.

In particular embodiments, the percentage of positive flows ("PPF") (such as, the percentage of positive nucleotide incorporation events based on the total number of nucleotide flows) can be evaluated over a given number of nucleotide flows, for example, the first 30 nucleotide flows, the first 40 nucleotide flows, the first 60 nucleotide flows, or the first 75 nucleotide flows. Subsequently, a PPF threshold can be set to exclude reads having a PPF greater than the threshold value. For example, in certain embodiments, if the PPF value is greater than about 60%, or greater than about 65% or greater than about 70%, the read can be excluded from the set of reads for further analysis, for example, alignment, and/or before writing out to an SFF or FASTQ file. It should be understood that where a particular read does not have the minimum number of nucleotide flows to meet the nucleotide flow number threshold, the actual number of nucleotide flows can be used to calculate the PPF and determine whether to filter the read.

In addition, certain reads can have a PPF that is below the expected value, which also can result in such a read being filtered. Thus, in various embodiments of the present methods, a read can be identified as acceptable if the read has a PPF between about 40% to about 60%, between about 45% to about 55%, between about 35% to about 65%, and between about 30% to about 70%, including various combinations of upper and lower thresholds as dictated by the particular application and run.

In some embodiments, test fragments can be excluded from read filtering based on the PPF. Test fragment sequences often are designed with sequences that typically do not occur naturally and therefore, can result in a large PPF. Accordingly, the methods of the present teachings permit the identification of such test fragments but do not filter the corresponding reads from a set of filtered reads.

It should be understood that in some limited embodiments, it is possible for the methods of the present teachings to filter from further processing certain possibly useful nucleic acid sequences using the PPF filter. For example, a long sample nucleic acid template which has a repeating sequence that is exactly the same as the nucleotide flow order (e.g., TACG) would be expected to have a positive nucleotide incorporation event for every nucleotide flow (theoretically, a PPF of 100%). Because of the large PPF, the hypothetical, long sample nucleic acid template would be identified as a mixed nucleic acid template read and filtered. Although such a piece of information may be unused or under-utilized, in practice, such sequences should be very rare and the benefits of generally excluding low quality reads resulting from mixed nucleic acid templates based on a threshold PPF are favored over excluding a very small proportion of genuine reads.

As for other criteria for read filtering, in various embodiments, read filtering can include targeted removal of reads that are generally a poor fit to the base calling model's expectations for high quality data. A typical or "well-behaved" read can be modeled and will have certain expectations about its signal distribution. For example, after the amount of incomplete extension ("IE") and carry forward ("CF") phasing effects have been estimated, certain expectations are present for how signals in neighboring nucleotide flows should be elevated or depressed. For example, when a positive IE is in effect, a large homopolymer sequence should result in a depressed signal in the nucleotide flow corresponding to the homopolymer while an elevated signal should be present in the next nucleotide flow of the same nucleotide.

In some embodiments, an observed signal can be compared to an expected signal based on a prediction of a base calling model for each nucleotide flow for each read. The difference between the observed signal and the predicted signal can be referred to as the flow residual for the well and nucleotide flow in question (e.g., flow residual equals observed signal minus predicted signal). In general, a high quality read which is well-described by the base calling model and the nucleic acid sequence that it estimates should have a low residual value.

More particularly, in certain embodiments, the median absolute value of the flow residual values over a number of initial nucleotide flows can be tracked for each read as a measure of the agreement between the observed data and the base calling model. If the median absolute flow residual value of a read is greater than a predefined threshold, then the read can be considered unreliable and it can be filtered and excluded from further processing. For example, in particular embodiments, the median absolute flow residual value can be determined over the first 30 nucleotide flows, the first 40 nucleotide flows, the first 50 nucleotide flows, the first 60 nucleotide flows or the first 70 nucleotide flows. In some embodiments, if the median absolute flow residual value is above a threshold of about 0.1, about 0.12, about 0.13, about 0.15, or about 0.2, or greater, the read can be filtered from the set of reads. For these criteria, a median absolute flow residual value filter can be applied to reads of both library fragments and test-fragments.

In addition to the above, other characteristics of reads can be identified and evaluated to determine whether the read should be filtered as being of low quality. For example, the strength of the signal from a particular well can be evaluated over the first two, three, or four key nucleotides. A key nucleotide can be a nucleotide that is present in a library sequencing key or a test fragment sequencing key. For wells that do not produce a strong signal across each of the predetermined number of (key) nucleotides, the read resulting from that well can be filtered.

For various embodiments, a read can be required to contain a minimum number (threshold) of base calls (nucleotides) to avoid identification as a low quality read. For example, a threshold read length can be at least 6 bases, at least 8 bases, at least 10 bases, at least 12 bases, at least 15 bases, at least 20 bases, or at least 25 bases, or more. If a read does not contain the threshold read length, the read can be filtered from the set of reads for further processing.

Further, in certain embodiments where sequencing keys are used, a read filter can require an exact match of a sequence of the read to the corresponding library sequencing key for that run. If an exact match is not identified, the read can be filtered.

Trimming Base Calls

In various embodiments, rather than filtering a read in its entirety, a read can be trimmed, such as having one or more nucleotides (base calls) excised or removed from the read, until an acceptable level of quality persists for the remaining portion of the read, which can be used in further processing and/or written to a SFF or FASTQ file. For example, a read that contains an adapter sequence (e.g., a B-adapter) can be trimmed to remove the adapter sequence (base calls) as well as any other base calls determined to be of low quality. Read trimming usually occurs at the 3' end of a read. However, in certain embodiments, base calls at the 5' end of a read can be trimmed, for example, where the base calls correspond to a sequencing key such as a library sequencing key.

As with other filters, each read trimming filter independently can be applied and the resulting, trimmed read length used in further processing or written to an appropriate file can be the sequence with the shortest length, which should contain only high quality base calls based on the filtering criteria. If the resulting trimmed read length is shorter than the threshold read length (as discussed above in connection with read filtering), the read can be filtered out entirely.

In various embodiments, a read can be examined to determine if an adapter (sequence) or a portion thereof can be identified with high confidence within a read. If a sequence matching an adapter sequence is found, the read can be trimmed to the base call (nucleotide) immediately prior to the start of the adapter.

In particular embodiments, searching a read for a match to a known adapter sequence can be done in flow-space using flow-space vectors. More specifically, the effects of CF and IE can be reversed to produce a phase-corrected ionogram (which can be stored in a SFF file). If a read extends into the adapter sequence, the 3' end of the phase-corrected ionogram can exhibit a pattern that is characteristic of the adapter sequence. In some embodiments, the method includes testing each position of the phase-corrected ionogram to determine whether it matches the pattern expected for the adapter sequence. Testing can include computing the Euclidean distance between the phase-corrected ionogram at the test position and the known ionogram for the adapter. If the distance falls below an adapter ionogram distance threshold, the corresponding position (translated from flow-space format back to base-space format) can be marked and/or recorded as an adapter trim location. If the distance does not fall below the adapter ionogram distance threshold, that position of the read does not match to the adapter sequence. In particular embodiments, the adapter ionogram distance threshold is a Euclidean distance of 5. However, depending on the application, the adapter ionogram distance threshold can be a distance of 2, 3, 4, 6, 7, 8, 9, or more.

In certain embodiments, lower quality base calls at the 3' end of a read can be trimmed. Considering the distribution of per base quality scores within a read, the highest quality base calls tend to occur at the start of the read, where phase errors typically are the smallest in magnitude. For a read that contains low quality base calls before reaching the end of a sequence of a sample nucleic acid template, the lower quality base calls at the 3' end can be trimmed. The trimming of low quality base calls at the 3' end of a read can performed using a per base quality score threshold.

In particular embodiments, base call trimming using a per base quality score can include scanning along the base calls of a read and computing a moving average in a fixed-length base call window along the read. A read trim point can be set to trim the earliest (5'-most) base call at which the moving average of the per base quality score drops below a moving average base quality score threshold. In certain embodiments, the base call window size is 30 base calls and the moving average base quality score threshold, below which trimming will occur, is a quality score of nine. Of course, depending upon the particular run and application, the window size can be five base calls, 10 base calls, 15 base calls, 20 base calls, 25 base calls, 35 base calls, or 40 base calls, or more. The moving average base quality score threshold also can vary depending on many factors and can be a quality score of 5, 6, 7, 8, 10, 11, 12, 13, 14, or 15, or more.

In particular embodiments, a read filter module can receive an SFF file. The read filter module can store, transmit and/or output trimmed reads and/or a filtered set of reads, and related data and information (for example, for each read, an adapter marker, a sequence key, and/or threshold and quality markers such as per base quality scores, indications of cuts to the reads, and/or the thresholds used in analysis of the data) in SFF or FASTQ file format as well as in a Sequence Alignment/Map ("SAM") file.

Alignment Module

An alignment module or aligner generally is configured to align the reads of a plurality of sample nucleic acid templates to determine a longer portion of a sample nucleic acid sequence. Although the overall goal typically is to identity the longer portion of the sample nucleic acid sequence, a first step usually is the identification of the nucleic acid sequences of sample nucleic acid templates or fragments (reads) in the wells. Reads may be assembled using the BFAST aligner or the Torrent Mapping Alignment Program ("TMAP") aligner, which can be used specifically with data and signals generated using nucleotide flow methodologies.

The aligner can accept as inputs some or all of the reads, for example, a set of filtered reads received from the read filter module. The aligner also can input and/or use a reference genome and index files to facilitate alignment and/or to control quality.

With respect to nucleotide flow methodologies and as discussed herein, the nucleotide flow order and the strength of the respective signal from each nucleotide flow can generate a putative nucleic acid sequence or read for the particular sample nucleic acid template in a well from which the signals were generated. However, because nucleic acid sequencing technologies can create relatively short reads of from ten to a few hundred bases in length, alignment of such reads in a practical time, especially when considering a complete genome, is a significant challenge. Accordingly, methods and algorithms can be used that reduce the size or complexity of the search target for aligning a particular read. For example, a read or putative nucleic acid sequence (also known as a query sequence or query nucleic acid sequence) can be passed through an index of a reference genome or alternatively, by indexing the reads and searching a reference genome. As a result of indexing, candidate alignment locations ("CALs") or candidate mapping locations ("CMLs") can be identified and used to perform local alignment analyses. In certain embodiments, the CAL or CML can be referred to a candidate reference nucleic acid sequence, which can be useful in determining the sequence of the sample nucleic acid template.

In some embodiments, more than one algorithm can be used to identify a candidate reference nucleic acid sequence. Algorithms that can be used in connection with the present teachings include, but are not limited to, Burrows-Wheeler Aligner ("BWA")-short (Li and Durbin, *Bioinformatics* 25, 14:1754-1760 (2009)), BWA-long (Li and Durbin, *Bioinformatics* 26, 5:589-595 (2010)), and Sequence Search and Alignment by Hashing Algorithm ("SSAHA") (Ning, Cox and Mullikin, *Genome Research* 11, 10:1725-1729 (2001)). In various embodiments, to take advantage of the strengths of each algorithm, two of the three or all three of these algorithms can be used in an alignment strategy to identify a list of at least one, or one or more, candidate reference nucleic acid sequences. For example, BWA-short quickly can map near-perfect reads while BMA-long and the SSAHA variant can sensitively map less similar and longer reads. Of course, other relevant algorithms can be used instead or to supplement the ones specifically mentioned.

In various embodiments, reads not mapped in a first stage can be mapped with a new set of algorithms and parameters in a second stage. In certain embodiments, the second stage uses the same algorithm(s) as the first stage, but with different parameters. In such circumstances, a two-stage mapping or alignment process can permit the majority of reads to be mapped or aligned with a fast set of algorithms and parameters while leaving difficult to map or align reads for a second round, which can use more sensitive algorithms and parameters.

After a candidate reference nucleic acid sequence is identified, it can be aligned against the putative nucleic acid sequence using a local sequence aligning method, for example, a Smith-Waterman algorithm (see, e.g., Smith and Waterman, *Journal of Molecular Biology* 147 (10:195-197 (1981)). The resulting alignments can be aggregated to determine the best mapping(s) or goodness of fit.

In some embodiments and with particular reference to data relating to nucleotide flow methodologies, a challenge exists to avoid miscalling homopolymer lengths as insertion and deletion ("indels") errors can occur during alignment and post-processing. For example, when the signal from one nucleotide flow falls between the values for one nucleotide incorporation event and two nucleotide incorporation events, it is uncertain whether the putative nucleic acid sequence should include one or two of the nucleobases in its sequence. A Smith-Waterman algorithm as described above normally cannot account for such homopolymer differences. To address this problem, the present teachings provide methods and systems where a putative nucleic acid sequence and a candidate reference nucleic acid sequence can be aligned using a third dimension.

More specifically, a three-dimensional matrix can be formed by using a Smith-Waterman algorithm to create a two-dimensional matrix where one axis is the nucleobases of the candidate reference nucleic acid sequence and the other axis is the length of the homopolymer or homopolymer number (e.g., "L" as used in the example below). That is, to account for all possible homopolymers during a single nucleotide flow, an alignment strategy can be implemented that accounts for all or at least a reasonable number of homopolymers lengths, where L equals zero means no nucleobase present (a non-incorporation event for that nucleotide flow), L equals one means one nucleobase is present (one nucleotide incorporation event occurred), L equals two means that two of the nucleobases in that particular nucleotide flow were incorporated, and so on. Accordingly, in some embodiments, a matrix can be created in which the length of the homopolymer on one axis is from zero to three, from zero to five, from zero to seven, from zero to ten, and so on with any reasonable number of homopolymer length as a variable.

As is familiar with a Smith-Waterman algorithm, various scores are attributed to different occurrences and overlaps of the nucleobases being compared. For example, the scores can include a match score or a match parameter value, a non-match score or a non-match parameter value, and a gap score or gap parameter value. The non-match score and the gap score can be negative values as they can be considered penalties. Other scores and parameters can be used depending on the particular application. For example, a flow penalty can be used to weight values in the matrices. Moreover, while the same scores and parameters can be used in name, the values of these scores and parameters can vary depending on the particular application and other variables.

Finally, the third dimension across which the above-described two-dimensional matrix is created and extended is the nucleotide flow order. That is, for a particular nucleotide flow, the above-described two-dimensional Smith-Waterman algorithm is created using the particular nucleobase of the nucleotide flow as the parameter against which to determine whether a match or mismatch occurred with respect to each nucleobase of the candidate reference nucleic acid sequence. In other words, for a first nucleotide flow, a two-dimensional matrix can be generated using a Smith-Waterman algorithm where the axes are L=0-10 and the specific nucleobases of the candidate reference nucleic acid sequence. Next, for a second nucleotide flow, another two-dimensional matrix can be generated using the Smith-Waterman algorithm where the axes remain as L=0-10 and the specific nucleobases of the candidate reference nucleic acid sequence. However, the second nucleotide flow likely will be of a different nucleotide such that the analysis and values in the cells of the matrix will vary as the comparison against the candidate reference nucleic acid sequence will be different.

Figure 5:
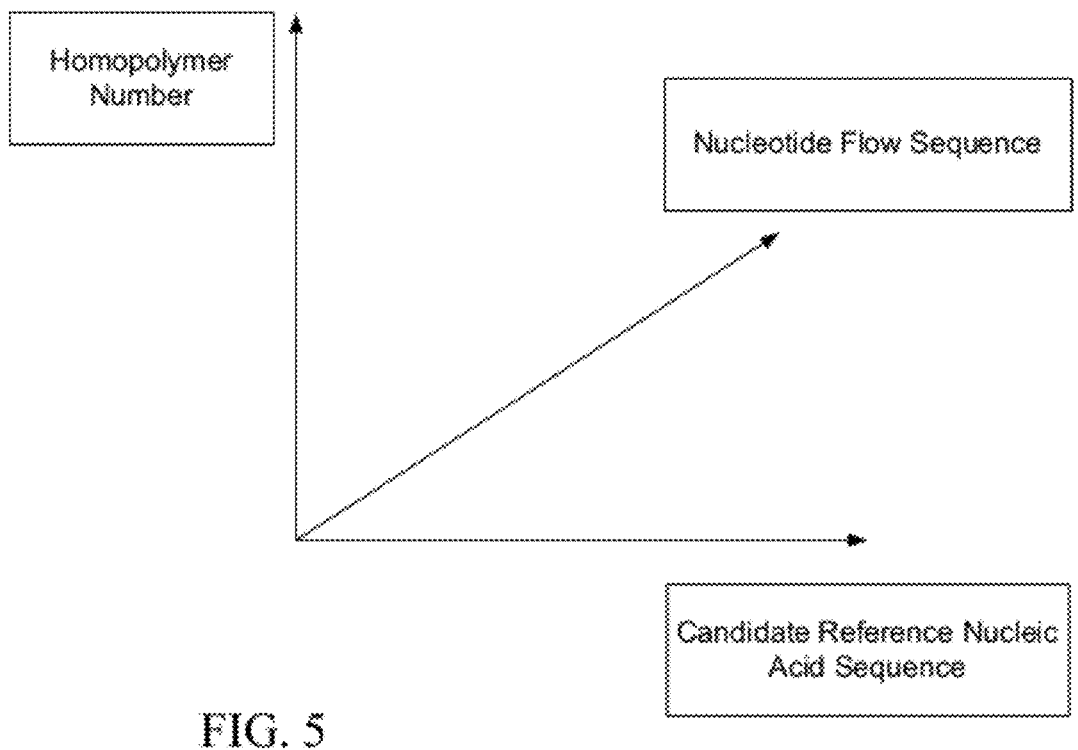
FIG. 5 is a schematic diagram depicting an exemplary three-dimensional matrix for use in alignment methodologies of the present teachings.

FIG. 5 depicts a three-dimensional axes system where each of the parameters discussed above can be visualized as creating a three-dimensional matrix having cells corresponding to the values determined by a Smith-Waterman algorithm. Visualized another way, the three-dimensional matrix can be viewed as stacked Smith-Waterman matrices.

After such a three-dimensional matrix is generated, methods of the present teachings include tracing back through each of the two-dimensional matrices for each of the nucleobases of the series of nucleotide flows to determine a goodness of fit. That is, similar to the movement through a Smith-Waterman matrix from one corner to the opposite, diagonal corner to determine an alignment fit, a trajectory is traced from one corner of the three-dimensional matrix to the opposite, diagonal corner. In certain embodiments, the goodness of fit is determined against the putative nucleic acid sequence. In particular embodiments, the goodness of fit is determined against the sample nucleic acid template. In some embodiments, the goodness of fit is determined against both the putative nucleic acid sequence and the sample nucleic acid template.

In various embodiments, after creating a two-dimensional matrix of homopolymer number and the nucleobases of the candidate reference nucleic acid sequence, the values in the cells can be weighted in response to the signal of the nucleobase of the nucleotide flow. That is, to account for the various lengths of homopolymer stretches that may be present in a putative nucleic acid sequence, the value of the homopolymer length can vary greatly, for example, from L=0-10. However, if the signal from a particular nucleotide flow is near zero, the likelihood that a non-incorporation event occurred is high. Accordingly, as the value of L becomes larger, it is less likely that the nucleobase was incorporated multiple times. Therefore, a weighting function can be used to account for such deviation from the observed signal.

In various embodiments, the generation of the matrices can be simplified by using information from the immediately prior matrix so as to collapse some of the data together. For example, after a first matrix of the nucleobases of a candidate reference nucleic acid sequence versus homopolymer number is generated for a first nucleotide flow, the highest number in each column (corresponding to the nucleobases) can be used as the top row (corresponding to L=0) in the matrix for a second nucleotide flow, and so on.

In some embodiments, more than one candidate reference nucleic acid sequence is identified. In such circumstances, the alignment analysis can be done against each of the candidate reference nucleic acid sequences. Each analysis can provide an alignment score, which can be indicative of goodness of fit to each of the candidate reference nucleic acid sequences thereby providing the most likely match or alignment of the putative nucleic acid sequence and/or the sample nucleic acid template. An alignment score can be the score of the cell or cells where the tracing or backtracking through the matrix or matrices begins, which score can include the sum of all or a portion of the cells through which the trajectory leads.

The following example is for illustration purposes only and should be considered non-limiting. However, the following example can be useful in understanding the specifics of the alignment methodologies described herein.

Example 3

For the purposes of this example, the nucleotide flow order is:

ACTGACTGA and the respective signals generated by a well after each nucleotide flow are:

0.1, 0.3, 0.2, 1.4, 0.3, 1.2, 0.8, 1.5, 0.7.

Based on the nucleotide flow sequence, a putative nucleic acid sequence is generated using the signals rounded to the nearest integer (as either a nucleotide incorporation event occurred or did not occur, but not partially). Thus, the above nucleotide flow order and signals establish a putative nucleic acid sequence as follows:

| FLOW SEQUENCE | | PUTATIVE SEQUENCE |
|---|---|---|
| A | 0.1 | |
| C | 0.3 | |
| T | 0.2 | |
| G | 1.4 | → G |
| A | 0.3 | |
| C | 1.2 | → C |
| T | 0.8 | → T |
| G | 1.5 | → G |
| A | 0.7 | → A |

In sum, the putative nucleic acid sequence (with associated signal in parentheses) becomes: G (1.4), C (1.2), T (0.8), G (1.5), and A (0.7), or GCTGA (without the signal values).

For the purpose of this example, assume that the candidate reference nucleic acid sequence is identified to be: GCTGGA.

First, the degree of fit or goodness of fit between each of the putative nucleotides of the read and the nucleotides of the candidate reference nucleic acid sequence is determined using a Smith-Waterman algorithm in which the value of a given cell in the matrix (e.g., $Cell_{i,j}$) is:

($Cell_{i,j}$)=maximum of:

$Cell_{i-1,j-1}$+score or $Cell_{i-1,j}$+gap penalty or $$\text{Cell}_{i,j-1} + \text{gap penalty},$$

where i is in the direction of the candidate reference nucleic acid sequence (across in this example) and j is in the direction of the putative nucleic acid sequence (down in this example).

The score is determined by whether a given nucleotide of the putative nucleic acid sequence is a match or a mismatch to the corresponding nucleotide of the candidate reference nucleic acid sequence as determined by which cell of the matrix is being considered. Further, an evaluation against an adjacent vertical cell ($\text{Cell}_{i,j-1}$) is given a gap penalty of −7 and an evaluation against an adjacent horizontal cell ($\text{Cell}_{i-1,j}$) is given a gap penalty of −7. Finally a flow penalty, which will be described later, is given a value of −5.

A matrix first is formed with the candidate reference nucleic acid sequence to be examined along the top and the putative nucleic acid sequence down the side.

```
              G  C  T  G  G  A     (reference)
(putative)    G
              C
              T
              G
              A
```

First, because the alignment is of the full sequences, multiples of the gap penalties (−7) for each entry in the first row and each entry in the first column are set. Each row entry is designated (S) because the entry corresponds to a start position.

G). As the cells are filled in, a letter after the value indicates from where the value was derived. For example, an M (match or mismatch) indicates the value was derived from the diagonally adjacent cell; a D (deletion) indicates that the value was derived from the adjacent horizontal cell; and an I (insertion) indicates that the value was derived from the adjacent vertical cell. The letters are useful as they can guide a path or trajectory back through the matrix.

First, looking at the diagonally adjacent cell, up and to the left:

$$\text{Cell}_{i-1,j-1} + \text{score} = 0 \text{ (for the } \text{Cell}_{i-1,j-1}) + 5 \text{ (for match of putative G to reference G)} = 5.$$

Next looking to the horizontal cell to the left:

$$\text{Cell}_{i-1,j} + \text{gap penalty} = -7 \text{ (for } \text{Cell}_{i-1,j}) - 7 = -14.$$

Next looking to the vertical cell above:

$$\text{Cell}_{i,j-1} + \text{gap penalty} = -7 \text{ (for } \text{Cell}_{i,j-1}) - 7 = -14.$$

Thus the maximum of these three calculations is 5, so the value of $\text{Cell}_{i,j} = 5$. An M is placed after the value to indicate that the value was derived from the diagonally adjacent cell.

|  |  | G | C | T | G | G | A | (reference) |
|---|---|---|---|---|---|---|---|---|
|  |  | 0 (S) | −7 (S) | −14 (S) | −21 (S) | −28 (S) | −35 (S) | −42 (S) |
| (putative) | G | −7 (S) | ☐ |  |  |  |  |  |
|  | C | −14 (S) |  |  |  |  |  |  |
|  | T | −21 (S) |  |  |  |  |  |  |
|  | G | −28 (S) |  |  |  |  |  |  |
|  | A | −35 (S) |  |  |  |  |  |  |

Moving from left to right, the first cell (shown as an empty box above) is evaluated for (putative-G) against (reference-

|  |  | G | C | T | G | G | A | i→ |
|---|---|---|---|---|---|---|---|---|
|  |  | 0 (S) | −7 (S) | −14 (S) | −21 (S) | −28 (S) | −35 (S) | −42 (S) |
| ↓ | G | −7 (S) | 5 (M) |  |  |  |  |  |
|  | C | −14 (S) |  |  |  |  |  |  |
|  | T | −21 (S) |  |  |  |  |  |  |

|   |   | G | C | T | G | G | A | i→ |
|---|---|---|---|---|---|---|---|---|
| G | −28 (S) |   |   |   |   |   |   |   |
| A | −35 (S) |   |   |   |   |   |   |   |

The next cell (indicated by the empty box below) is (putative-C) against (reference-G).

|   |   |   | G | C | T | G | G | A | i→ |
|---|---|---|---|---|---|---|---|---|---|
|   |   | 0 (S) | −7 (S) | −14 (S) | −21 (S) | −28 (S) | −35 (S) | −42 (S) |   |
| ↓ | G | −7 (S) | 5 (M) |   |   |   |   |   |   |
|   | C | −14 (S) | ☐ |   |   |   |   |   |   |
|   | T | −21 (S) |   |   |   |   |   |   |   |
|   | G | −28 (S) |   |   |   |   |   |   |   |
|   | A | −35 (S) |   |   |   |   |   |   |   |

To find its value, again calculate the value by evaluating the diagonal cell:

$Cell_{i-1,j-1}+score=-7$ (for $Cell_{i-1,j-1}$)+(−4 mismatch of putative-C and reference-G)=−11.

Calculating the value against the adjacent horizontal cell:

$Cell_{i-1,j}+gap\ penalty=-14$ ($Cell_{i-1,j}$)−7 (gap penalty)=−21.

Finally looking at the adjacent vertical cell:

$Cell_{i,j-1}+gap\ penalty=5$ ($Cell_{i,j-1}$)−7 (gap penalty)=−2.

So the value of the cell is −2 and it has an I after it because the value was derived from the adjacent vertical cell.

|   |   |   | G | C | T | G | G | A | i→ |
|---|---|---|---|---|---|---|---|---|---|
|   |   | 0 (S) | −7 (S) | −14 (S) | −21 (S) | −28 (S) | −35 (S) | −42 (S) |   |
| ↓ | G | −7 (S) | 5 (M) |   |   |   |   |   |   |
|   | C | −14 (S) | −2 (I) |   |   |   |   |   |   |
|   | T | −21 (S) |   |   |   |   |   |   |   |
|   | G | −28 (S) |   |   |   |   |   |   |   |
|   | A | −35 (S) |   |   |   |   |   |   |   |

Continuing to move down the first column (reference-G), the next cell, indicated by the box, is:

|   |   | G | C | T | G | G | A | i→ |
|---|---|---|---|---|---|---|---|---|
|   | 0 (S) | −7 (S) | −14 (S) | −21 (S) | −28 (S) | −35 (S) | −42 (S) |   |
| G | −7 (S) | 5 (M) | 0 |   |   |   |   |   |
| C | −14 (S) | −2 (I) |   |   |   |   |   |   |
| T | −21 (S) | ☐ |   |   |   |   |   |   |
| G | −28 (S) |   |   |   |   |   |   |   |
| ↓ A | −35 (S) |   |   |   |   |   |   |   |

This cell is (putative-A) evaluated against (reference-G). For this cell, the algorithm yields:

$Cell_{i-1,j-1}$+score=−14 (for $Cell_{i-1,j-1}$)+(−4 mismatch of (putative-A) and (reference-G)=−18.

$Cell_{i-1,j}$+gap penalty=−21 ($Cell_{i-1,j}$)−7 (gap penalty)=−28.

$Cell_{i,j-1}$+gap=−2 ($Cell_{i,j-1}$)−7 (gap penalty)=−9.

So the value of the cell is −9 and the value has an I after it as the value was derived from the adjacent vertical cell.

Proceeding down the column in the same manner, the complete column for the first reference-G looks like:

|   |   |        | G      | C       | T       | G       | G       | A       | i→ |
|---|---|--------|--------|---------|---------|---------|---------|---------|----|
|   |   | 0 (S)  | −7 (S) | −14 (S) | −21 (S) | −28 (S) | −35 (S) | −42 (S) |    |
|   | G | −7 (S) | 5 (M)  | 0       |         |         |         |         |    |
|   | C | −14 (S)| −2 (I) |         |         |         |         |         |    |
|   | T | −21 (S)| −9 (I) |         |         |         |         |         |    |
|   | G | −28 (S)| −16 (M)|         |         |         |         |         |    |
| j↓| A | −35 (S)| −23 (I)|         |         |         |         |         |    |

The next column is reference-C, with the first cell against putative-G.

|   |   |        | G      | C       | T       | G       | G       | A       | i→ |
|---|---|--------|--------|---------|---------|---------|---------|---------|----|
|   |   | 0 (S)  | −7 (S) | −14 (S) | −21 (S) | −28 (S) | −35 (S) | −42 (S) |    |
|   | G | −7 (S) | 5 (M)  |         |         |         |         |         |    |
|   | C | −14 (S)| −2 (I) |         |         |         |         |         |    |
|   | T | −21 (S)| −9 (I) |         |         |         |         |         |    |
|   | G | −28 (S)| −16 (M)|         |         |         |         |         |    |
| j↓| A | −35 (S)| −23 (I)|         |         |         |         |         |    |

Because putative-G and reference-C do not match, the score is −4. Looking at the diagonally adjacent cell, $Cell_{i,j}$, becomes: $Cell_{i-1,j-1}$+score=−7+−4=−11.

Looking next at the horizontal and vertical cells:

$Cell_{i-1,j}$+gap penalty=5−7=−2

$Cell_{i,j-1}$+gap penalty=−14−7=−21

The maximum of the three calculations is −2 and therefore, the cell value is −2, with a D after it to indicate that the value was derived from the adjacent horizontal cell.

|   |   |        | G      | C       | T       | G       | G       | A       | i→ |
|---|---|--------|--------|---------|---------|---------|---------|---------|----|
|   |   | 0 (S)  | −7 (S) | −14 (S) | −21 (S) | −28 (S) | −35 (S) | −42 (S) |    |
|   | G | −7 (S) | 5 (M)  | −2 (D)  |         |         |         |         |    |
|   | C | −14 (S)| −2 (I) |         |         |         |         |         |    |
|   | T | −21 (S)| −9 (I) |         |         |         |         |         |    |
|   | G | −28 (S)| −16 (M)|         |         |         |         |         |    |
| j↓| A | −35 (S)| −23 (I)|         |         |         |         |         |    |

Next looking at the cell for putative-C and reference-C shown in the block below:

|   |   | G | C | T | G | G | A | i→ |
|---|---|---|---|---|---|---|---|---|
|   |   | 0 (S) | −7 (S) | −14 (S) | −21 (S) | −28 (S) | −35 (S) | −42 (S) |
|   | G | −7 (S) | 5 (M) | −2 (D) |   |   |   |   |
|   | C | −14 (S) | −2 (I) | ☐ |   |   |   |   |
|   | T | −21 (S) | −9 (I) |   |   |   |   |   |
|   | G | −28 (S) | −16 (M) |   |   |   |   |   |
| j↓ | A | −35 (S) | −23 (I) |   |   |   |   |   |

Because putative-C and reference-C match, the score is 5. Looking at the diagonally adjacent cell, the $\text{Cell}_{i,j}$ becomes:

$$\text{Cell}_{i-1,j-1} + \text{score} = 5+5 = 10$$

Looking next at the horizontal and vertical cells:

$$\text{Cell}_{i-1,j} + \text{gap penalty} = -2-7 = -9$$

$$\text{Cell}_{i,j-1} + \text{gap penalty} = -2-7 = -9$$

The maximum of the three calculations is 10 and therefore, the cell value is 10, with an M after it to indicate that the value was derived from the diagonally adjacent cell.

|   |   | G | C | T | G | G | A | i→ |
|---|---|---|---|---|---|---|---|---|
|   |   | 0 (S) | −7 (S) | −14 (S) | −21 (S) | −28 (S) | −35 (S) | −42 (S) |
|   | G | −7 (S) | 5 (M) | −2 (D) |   |   |   |   |
|   | C | −14 (S) | −2 (I) | 10 (M) |   |   |   |   |
|   | T | −21 (S) | −9 (I) |   |   |   |   |   |
|   | G | −28 (S) | −16 (M) |   |   |   |   |   |
| j↓ | A | −35 (S) | −23 (I) |   |   |   |   |   |

The next cell in the next column has reference-T against=putative-G:

|   |   | G | C | T | G | G | A | i→ |
|---|---|---|---|---|---|---|---|---|
|   |   | 0 (S) | −7 (S) | −14 (S) | −21 (S) | −28 (S) | −35 (S) | −42 (S) |
|   | G | −7 (S) | 5 (M) | −2 (D) | ☐ |   |   |   |
|   | C | −14 (S) | −2 (I) | 10 (M) |   |   |   |   |
|   | T | −21 (S) | −9 (I) |   |   |   |   |   |
|   | G | −28 (S) | −16 (M) |   |   |   |   |   |
| j↓ | A | −35 (S) | −23 (I) |   |   |   |   |   |

$$\text{Cell}_{i-1,j-1} + \text{score} = -14-4 = -18$$

$$\text{Cell}_{i-1,j} + \text{gap} = -2-7 = -9$$

$$\text{Cell}_{i,j-1} + \text{gap} = -21-7 = -28$$

Consequently, this cell becomes −9 (D).

|   |   | G | C | T | G | G | A | i→ |
|---|---|---|---|---|---|---|---|---|
|   |   | 0 (S) | −7 (S) | −14 (S) | −21 (S) | −28 (S) | −35 (S) | −42 (S) |
|   | G | −7 (S) | 5 (M) | −2 (D) | −9 (D) |   |   |   |
|   | C | −14 (S) | −2 (I) | 10 (M) |   |   |   |   |
|   | T | −21 (S) | −9 (I) |   |   |   |   |   |
|   | G | −28 (S) | −16 (M) |   |   |   |   |   |
| j↓ | A | −35 (S) | −23 (I) |   |   |   |   |   |

Looking at the next cell down:

|   |   | G | C | T | G | G | A | i→ |
|---|---|---|---|---|---|---|---|---|
|   |   | 0 (S) | −7 (S) | −14 (S) | −21 (S) | −28 (S) | −35 (S) | −42 (S) |
|   | G | −7 (S) | 5 (M) | −2 (D) | −9 (D) |   |   |   |
|   | C | −14 (S) | −2 (I) | 10 (M) | ☐ |   |   |   |
|   | T | −21 (S) | −9 (I) |   |   |   |   |   |
|   | G | −28 (S) | −16 (M) |   |   |   |   |   |
| j↓ | A | −35 (S) | −23 (I) |   |   |   |   |   |

$Cell_{i-1,j-1} + score = -2 - 4 = -6$ $Cell_{i-1,j} + gap = 10 - 7 = 3$ $Cell_{i,j-1} + gap = -9 - 7 = -16$ Consequently, this cell is 3 (D).

|   |   | G | C | T | G | G | A | i→ |
|---|---|---|---|---|---|---|---|---|
|   |   | 0 (S) | −7 (S) | −14 (S) | −21 (S) | −28 (S) | −35 (S) | −42 (S) |
|   | G | −7 (S) | 5 (M) | −2 (D) | −9 (D) |   |   |   |
|   | C | −14 (S) | −2 (I) | 10 (M) | 3 (D) |   |   |   |
|   | T | −21 (S) | −9 (I) |   |   |   |   |   |
|   | G | −28 (S) | −16 (M) |   |   |   |   |   |
| j↓ | A | −35 (S) | −23 (I) |   |   |   |   |   |

In sum, each iteration of the analysis method or algorithm looks at:

1) the immediate preceding value on the diagonal and adds the appropriate score;
2) the value in the immediate proceeding vertical cell and adds the gap penalty;
3) the value in the immediate preceding horizontal cell and adds the gap penalty; and from these values, the most positive calculated value for the cell is used.

Doing this for the rest of the matrix results in:

|   |   | G | C | T | G | G | A | i→ |
|---|---|---|---|---|---|---|---|---|
|   |   | 0 (S) | −7 (S) | −14 (S) | −21 (S) | −28 (S) | −35 (S) | −42 (S) |
|   | G | −7 (S) | 5 (M) | −2 (D) | −9 (D) | −16 (M) | 23 (M) | −30 (D) |
|   | C | −14 (S) | −2 (I) | 10 (M) | 3 (D) | −4 (D) | −11 (D) | −18 (D) |
|   | T | −21 (S) | −9 (I) | 3 (I) | 15 (M) | 8 (D) | 1 (D) | −6 (D) |
|   | G | −28 (S) | −16 (M) | −4 (I) | 8 (I) | 20 (M) | 13 (M) | 6 (D) |
| j↓ | A | −35 (S) | −23 (I) | −11 (I) | 1 (I) | 13 (I) | 16 (M) | 18 (M) |

Next, to determine the alignment, a trajectory is traced back through the matrix working column-by-column, with the starting point being the cell with the highest value in the far right hand column. A path then is traced to the left using the letter designation to determine the direction of movement, such as left, diagonal, or up.

Here, the highest value in the far right column is 18 (M), which is a match of A. The M means that the next cell is the diagonally adjacent cell, which is 13 (M), a match for G. The M means that the next cell again is the diagonally adjacent cell, which is 8 (D). Here, no match is found but a deletion so that the sequence gets a dash and currently is: −G A.

Next, the D means that the next cell is the adjacent horizontal cell, which is 15 (M), a match for T. The M means that the next cell is the diagonally adjacent cell, which is 10 (M), a match for C. The M means that the next cell again is the diagonally adjacent cell, which is 5 (M), a match for G. Finally, the M again means that the next cell is the diagonally adjacent cell, which is 0 (S), the start cell. Consequently, the alignment using a Smith-Waterman algorithm provides the sequence: G C T-G A.

Thus, based on the Smith-Waterman algorithm, it is unclear whether a deletion is present in the putative nucleic acid sequence or a homopolymer stretch was miscalled.

Using an embodiment of an algorithm of the present teachings, a matrix of the candidate reference nucleic acid sequence is compared against the homopolymer number ("L") for each nucleotide of the nucleotide flow order thereby creating a three-dimensional matrix. For this example, L is set from zero to three to keep the example reasonable.

First, multiples of the gap penalties (−7) for each entry in the first row and each entry in the first column are set. Each row entry is designated (D) because the entry corresponds to a deletion and each column entry is designated (I) because the entry corresponds to an insertion. The number after the letter in parentheses indicates the homopolymer row in which it is located, for example, a zero indicates that its associated value is in the L=0 row of homopolymers.

|  |  | G | C | T | G | G | A |
|---|---|---|---|---|---|---|---|
| L = 0 | 0 | −7 (D0) | −14 (D0) | −21 (D0) | −28 (D0) | −35 (D0) | −42 (D0) |
| L = 1 | −7 (I) |  |  |  |  |  |  |
| L = 2 | −14 (I) |  |  |  |  |  |  |
| L = 3 | −21 (I) |  |  |  |  |  |  |

The first nucleotide in the nucleotide flow sequence is (A), which has a signal value of (0.1). The flow order nucleotide (A) is not a match for the candidate reference nucleic acid sequence nucleotide (G). Using the Smith-Waterman technique as described above, the first cell (shown as the box below) is given a score of −4 because of the mismatch.

| A = 0.1 |  |  |  |  |  |  |  |
|---|---|---|---|---|---|---|---|
|  |  | G | C | T | G | G | A |
| L = 0 | 0 | −7 (D0) | −14 (D0) | −21 (D0) | −28 (D0) | −35 (D0) | −42 (D0) |
| L = 1 | −7 (I) |  |  |  |  |  |  |
| L = 2 | −14 (I) |  |  |  |  |  |  |
| L = 3 | −21 (I) |  |  |  |  |  |  |

As a result, −4 is added to the adjacent diagonal cell above (0) and the $Cell_{i,j}$ becomes:

$Cell_{i-1,j-1}$+score=0−4=−4

$Cell_{i-1,j}$+gap penalty=−7−7=−14

$Cell_{i-1,j-1}$+gap penalty=−7−7=−14

Accordingly, the value for the cell is −4, with an (M) designation for its origin.

|  |  | A = 0.1 |  |  |  |  |  |
|---|---|---|---|---|---|---|---|
|  |  | G | C | T | G | G | A |
| L = 0 | 0 | −7 (D0) | −14 (D0) | −21 (D0) | −28 (D0) | −35 (D0) | −42 (D0) |
| L = 1 | −7 (I) | −4 (M) |  |  |  |  |  |
| L = 2 | −14 (I) |  |  |  |  |  |  |
| L = 3 | −21 (I) |  |  |  |  |  |  |

The next cell (shown by the box below) is assessed by comparing the flow nucleotide (A) again against the reference (G). Again there is no match so the score is −4 again.

| | | G | C | | T | G | G | A |
|---|---|---|---|---|---|---|---|---|
| A = 0.1 | | | | | | | | |
| L = 0 | 0 | -7 (D0) | -14 (D0) | | -21 (D0) | -28 (D0) | -35 (D0) | -42 (D0) |
| L = 1 | -7 (I) | -4 (M) | ☐ | | | | | |
| L = 2 | -14 (I) | | | | | | | |
| L = 3 | -21 (I) | | | | | | | |

$Cell_{i-1,j-1}$+score=−7 (diagonal cell)−4 (mismatch score)=−11

$Cell_{i-1,j}$+gap penalty=−4 (horizontal cell)−7 (gap penalty)=−11

$Cell_{i,j-1}$+gap penalty=−14 (vertical cell)−7 (gap penalty)=−21

So the cell is given a value of −11(M), due to the mismatch.

| | | G | C | | T | G | G | A |
|---|---|---|---|---|---|---|---|---|
| L = 0 | 0 | -7 (D0) | -14 (D0) | | -21 (D0) | -28 (D0) | -35 (D0) | -42 (D0) |
| L = 1 | -7 (I) | -4 (M) | -11 (M) | | | | | |
| L = 2 | -14 (I) | | | | | | | |
| L = 3 | -21 (I) | | | | | | | |

Continuing for the next cell:

| | | G | C | T | | G | G | A |
|---|---|---|---|---|---|---|---|---|
| A = 0.1 | | | | | | | | |
| L = 0 | 0 | -7 (D0) | -14 (D0) | -21 (D0) | | -28 (D0) | -35 (D0) | -42 (D0) |
| L = 1 | -7 (I) | -4 (M) | -11 (M) | ☐ | | | | |
| L = 2 | -14 (I) | | | | | | | |
| L = 3 | -21 (I) | | | | | | | |

$Cell_{i-1,j-1}$+score=−14 (diagonal cell)−4 (mismatch score)=−18

$Cell_{i-1,j}$+gap penalty=−11 (horizontal cell)−7 (gap penalty)=−18

$Cell_{i,j-1}$+gap penalty=−21 (vertical cell)−7 (gap penalty)=−28

Consequently, the cell has a value of −18 (M) (note that an M was designated rather than a D).

| A = 0.1 | | | | | | | |
|---|---|---|---|---|---|---|---|
| | | G | C | T | G | G | A |
| L = 0 | 0 | −7 (D0) | −14 (D0) | −21 (D0) | −28 (D0) | −35 (D0) | −42 (D0) |
| L = 1 | −7 (I) | −4 (M) | −11 (M) | −18 (M) | | | |
| L = 2 | −14 (I) | | | | | | |
| L = 3 | −21 (I) | | | | | | |

Continuing this way for the remaining entries, the matrix becomes:

| A = 0.1 | | | | | | | |
|---|---|---|---|---|---|---|---|
| | | G | C | T | G | G | A |
| L = 0 | 0 | −7 (D0) | −14 (D0) | −21 (D0) | −28 (D0) | −35 (D0) | −42 (D0) |
| L = 1 | −7 (I) | −4 (M) | −11 (M) | −18 (M) | −25 (M) | −32 (M) | −30 (M) |
| L = 2 | −14 (I) | −11 (M) | −8 (M) | −15 (M) | −22 (M) | −29 (M) | −27 (M) |
| L = 3 | −21 (I) | −18 (M) | −15 (M) | −12 (M) | −19 (M) | −26 (M) | −24 (M) |

Next each value is weighted by a function which takes into account how far the signal value (here A=0.1) is from the expected value (A=0). The function that is used should give the same number whether the signal is greater than or less than the putative value. The function also should take into account the fact that a homopolymer of length 3 is more unlikely than a homopolymer of length 2.

In one embodiment the weight factor is WF=abs(L-signal value)*flow penalty (wherein flow penalty=−5). So for L=0, WF=−abs(0−0.1)*(−5)=(−0.5) for each element in the table. Ignoring every other cell in the matrix except row L=0, the weighting factor −0.5 is added to each value in the L=0 row. The matrix row for L=0 then becomes (shown in grey):

| | | G | C | T | G | G | A |
|---|---|---|---|---|---|---|---|
| L = 0 | −0.5 (S0) | −7.5 (D0) | −14.5 (D0) | −21.5 (D0) | −28.5 (D0) | −35.5 (D0) | −42.5 (D0) |
| L = 1 | −7 (I) | −4 (M) | −11 (M) | −18 (M) | −25 (M) | −32 (M) | −30 (M) |
| L = 2 | −14 (I) | −11 (M) | −8 (M) | −15 (M) | −22 (M) | −29 (M) | −27 (M) |
| L = 3 | −21 (I) | −18 (M) | −15 (M) | −12 (M) | −19 (M) | −26 (M) | −24 (M) |

Repeating this for L=1, the weight factor becomes WF=−abs(1−0.1)*(−5)=(−4.5). Applying this to each entry in the L=1 row, the matrix becomes:

| | | G | C | T | G | G | A |
|---|---|---|---|---|---|---|---|
| L = 0 | −0.5 (S0) | −7.5 (D0) | −14.5 (D0) | −21.5 (D0) | −28.5 (D0) | −35.5 (D0) | −42.5 (D0) |
| L = 1 | −11.5 (I) | −8.5 (M) | −15.5 (M) | −22.5 (M) | −29.5 (M) | −36.5 (M) | −34.5 (M) |
| L = 2 | −14 (I) | −11 (M) | −8 (M) | −15 (M) | −22 (M) | −29 (M) | −27 (M) |
| L = 3 | −21 (I) | −18 (M) | −15 (M) | −12 (M) | −19 (M) | −26 (M) | −24 (M) |

Doing this for L=2 and L=3, the WF=−abs(2−0.1)*(−5)=(−9.5) and WF=−abs(3−0.1)*(−5)=(−14.5), respectively, the weighted matrix becomes:

| | G | C | T | G | G | A |
|---|---|---|---|---|---|---|
| | | | A = 0.1 | | | |
| L = 0 | −0.5 (S0) | −7.5 (D0) | −14.5 (D0) | −21.5 (D0) | −28.5 (D0) | −35.5 (D0) | −42.5 (D0) |
| L = 1 | −11.5 (I) | −8.5 (M) | −15.5 (M) | −22.5 (M) | −29.5 (M) | −36.5 (M) | −34.5 (M) |
| L = 2 | −23.5 (I) | −20.5 (M) | −17.5 (M) | −24.5 (M) | −31.5 (M) | −38.5 (M) | −36.5 (M) |
| L = 3 | −35.5 (I) | −32.5 (M) | −29.5 (M) | −26.5 (M) | −33.5 (M) | −40.5 (M) | −38.5 (M) |

Moving to the next nucleotide (C) in the flow order that had a signal of 0.3, the values of L=0 row are set to the highest scoring cell for each column of the previous nucleotide, in this case (A). The first column then is completed by adding the gap penalty beginning with the top cell value at L=0. Thus the highest values in each column of weighted matrix of the previous nucleotide flow are (shown in grey):

A = 0.1

| | G | C | T | G | G | A |
|---|---|---|---|---|---|---|
| L = 0 | −0.5 (S0) | −7.5 (D0) | −14.5 (D0) | −21.5 (D0) | −28.5 (D0) | −35.5 (D0) | −42.5 (D0) |
| L = 1 | −11.5 (I) | −8.5 (M) | −15.5 (M) | −22.5 (M) | −29.5 (M) | −36.5 (M) | −34.5 (M) |
| L = 2 | −23.5 (I) | −20.5 (M) | −17.5 (M) | −24.5 (M) | −31.5 (M) | −38.5 (M) | −36.5 (M) |
| L = 3 | −35.5 (I) | −32.5 (M) | −29.5 (M) | −26.5 (M) | −33.5 (M) | −40.5 (M) | −38.5 (M) |

Accordingly, the first L=0 row of the next matrix is:

C = 0.3

| | G | C | T | G | G | A |
|---|---|---|---|---|---|---|
| L = 0 | −0.5 (S0) | −7.5 (D0) | −14.5 (D0) | −21.5 (D0) | −28.5 (D0) | −35.5 (D0) | −34.5 (M1) |
| L = 1 | −7.5 (I) | | | | | | |
| L = 2 | −14.5 (I) | | | | | | |
| L = 3 | −21.5 (I) | | | | | | |

Moving to the next row and first column (shown as the box below), and again using the Smith-Waterman algorithm as before:

Cell$_{i-1,j-1}$+score=−0.5 (diagonal cell)−4 (mismatch score)=−4.5

Cell$_{i-1,j}$+gap penalty=−7.5 (horizontal cell)−7 (gap penalty)=−14.5

Cell$_{i,j-1}$+gap penalty=−7.5 (vertical cell)−7 (gap penalty)=−14.5

Thus the value of this cell is −4.5 and has an associated M.

C = 0.3

| | G | C | T | G | G | A |
|---|---|---|---|---|---|---|
| L = 0 | −0.5 (S0) | −7.5 (D0) | −14.5 (D0) | −21.5 (D0) | −28.5 (D0) | −35.5 (D0) | −34.5 (M1) |
| L = 1 | −7.5 (I) | −4.5 (M) | | | | | |
| L = 2 | −14.5 (I) | | | | | | |
| L = 3 | −21.5 (I) | | | | | | |

For the next entry for L=1 (shown in the box below), there is a match, so the score value would be (−7.5+5=−2.5), the vertical gap would be (−14.5−7=−21.5), and the horizontal gap would be (−4.5−7=−11.5) so (−2.5) is the maximum value as determined from the diagonally adjacent cell.

| | | C = 0.3 | | | | | |
|---|---|---|---|---|---|---|---|
| | G | C | | T | G | G | A |
| L = 0 | −0.5 (S0) | −7.5 (D0) | −14.5 (D0) | −21.5 (D0) | −28.5 (D0) | −35.5 (D0) | −34.5 (M1) |
| L = 1 | −7.5 (I) | −4.5 (M) | −2.5 (M) | | | | |
| L = 2 | −14.5 (I) | | | | | | |
| L = 3 | −21.5 (I) | | | | | | |

Continuing with the remaining cells, the completed matrix looks like:

| | | | C = 0.3 | | | | |
|---|---|---|---|---|---|---|---|
| | G | C | T | G | G | A | |
| L = 0 | −0.5 (S0) | −7.5 (D0) | −14.5 (D0) | −21.5 (D0) | −28.5 (D0) | −35.5 (D0) | −34.5 (M1) |
| L = 1 | −7.5 (I) | −4.5 (M) | −2.5 (M) | −9.5 (D) | −16.5 (D) | −23.5 (D) | −30.5 (D) |
| L = 2 | −14.5 (I) | −11.5 (M) | .5 (M) | −6.5 (M) | −13.5 (M) | −20.5 (M) | −27.5 (M) |
| L = 3 | −21.5 (I) | −18.5 (M) | −6.5 (I) | −3.5 (M) | −10.5 (M) | −17.5 (M) | −24.5 (M) |

Again each value is weighted by how far the signal value (here C=0.3) was from the expected value (C=0) according to the weight factor WF=−abs(L−sig)*flow penalty (where the flow penalty is −5). So for L=0, WF=−abs(0−0.3)*(−5)=(−1.5) for each element in that row of the matrix. For the remaining rows: L=1, 2, and 3, the weight factors become WF=−3.5, −8.5 and −13.5, respectively, and the completed weighted matrix becomes:

| | | | C = 0.3 | | | | |
|---|---|---|---|---|---|---|---|
| | G | C | T | G | G | A | |
| L = 0 | −2.0 (S0) | −9.0 (D0) | −16.1 (D0) | −23.0 (D0) | −30.0 (D0) | −37.0 (D0) | −36.0 (M1) |
| L = 1 | −11 (I) | −8.0 (M) | −6.0 (M) | −13.0 (D) | −20.0 (D) | −27.0 (D) | −34.0 (D) |
| L = 2 | −23.0 (I) | −20.0 (M) | −8.0 (M) | −15.0 (M) | −22.0 (M) | −29.0 (M) | −36.0 (M) |
| L = 3 | −35.0 (I) | −32.0 (M) | −20.0 (I) | −17.0 (M) | −24.0 (M) | −31.0 (M) | −38.0 (M) |

Selecting the highest values (shown in grey):

| | | C = 0.3 | | | | | |
|---|---|---|---|---|---|---|---|
| | G | C | T | G | G | A | |
| L = 0 | −2.0 (S0) | −9.0 (D0) | −16.0 (D0) | −23.0 (D0) | −30.0 (D0) | −37.0 (D0) | −36.0 (M1) |
| L = 1 | −11 (I) | −8.0 (M) | −6.0 (M) | −13.0 (D) | −20.0 (D) | −27.0 (D) | −34.0 (D) |
| L = 2 | −23.0 (I) | −20.0 (M) | −8.0 (M) | −15.0 (M) | −22.0 (M) | −29.0 (M) | −36.0 (M) |
| L = 3 | −35.0 (I) | −32.0 (M) | −20.0 (I) | −17.0 (M) | −24.0 (M) | −31.0 (M) | −38.0 (M) |

Moving to the next nucleotide of the nucleotide flow order, T, with a signal of 0.2, the L=0 row and first column become:

|       | T = 0.2    |            |            |             |             |             |             |
|-------|------------|------------|------------|-------------|-------------|-------------|-------------|
|       | G          | C          | T          | G           | G           | A           |             |
| L = 0 | −2.0 (S0)  | −8.0 (M1)  | −6.0 (M1)  | −13.0 (D1)  | −20.0 (D1)  | −27.0 (D1)  | −34.0 (D1)  |
| L = 1 | −9.0 (I)   |            |            |             |             |             |             |
| L = 2 | −16.0 (I)  |            |            |             |             |             |             |
| L = 3 | −23.0 (I)  |            |            |             |             |             |             |

Again using the Smith-Waterman algorithm as before, the completed matrix becomes:

|       | T = 0.2    |            |            |             |             |             |             |
|-------|------------|------------|------------|-------------|-------------|-------------|-------------|
|       | G          | C          | T          | G           | G           | A           |             |
| L = 0 | −2.0 (S0)  | −8.0 (M1)  | −6.0 (M1)  | −13.0 (D1)  | −20.0 (D1)  | −27.0 (D1)  | −34.0 (D1)  |
| L = 1 | −9.0 (I)   | −6.0 (M)   | −12.0 (M)  | −1.0 (M)    | −8.0 (D)    | −15.0 (D)   | −22.0 (D)   |
| L = 2 | −16.0 (I)  | −13.0 (M)  | −10.0 (M)  | −7.0 (M)    | −5.0 (M)    | −12.0 (M)   | −19.0 (M)   |
| L = 3 | −23.0 (I)  | −20.0 (M)  | −17.0 (M)  | −5.0 (M)    | −11.0 (M)   | −9.0 (M)    | −16.0 (M)   |

In this case, the weight factors for L=0, 1, 2, 3 are −1.0, −4.0, −9.0, and −14.0, respectively. Applying the weight factors, the weighted matrix becomes:

|       | T = 0.2    |            |            |             |             |             |             |
|-------|------------|------------|------------|-------------|-------------|-------------|-------------|
|       | G          | C          | T          | G           | G           | A           |             |
| L = 0 | −3.0 (S0)  | −9.0 (M1)  | −7.0 (M1)  | −14.0 (D1)  | −21.0 (D1)  | −28.0 (D1)  | −35.0 (D1)  |
| L = 1 | −13.0 (I)  | −10.0 (M)  | −16.0 (M)  | −5.0 (M)    | −12.0 (D)   | −19.0 (D)   | −26.0 (D)   |
| L = 2 | −25.0 (I)  | −22.0 (M)  | −19.0 (M)  | −16.0 (M)   | −14.0 (M)   | −21.0 (M)   | −28.0 (M)   |
| L = 3 | −37.0 (I)  | −34.0 (M)  | −31.0 (M)  | −19.0 (M)   | −25.0 (M)   | −23.0 (M)   | −30.0 (M)   |

This procedure is continued for each nucleotide in the nucleotide flow order to provide the following weighted matrices:

|           | G          | C          | T          | G           | G           | A           |             |
|-----------|------------|------------|------------|-------------|-------------|-------------|-------------|
| G = 1.4   |            |            |            |             |             |             |             |
| L = 0     | −10.0 (S0) | −16.0 (M0) | −14.0 (M0) | −12.0 (M1)  | −19.0 (D1)  | −26.0 (D1)  | −33.0 (D1)  |
| L = 1     | −12.0 (I)  | 0.0 (M)    | −7.0 (D)   | −13.0 (M)   | −2.0 (M)    | −9.0 (M)    | −16.0 (D)   |
| L = 2     | −20.0 (I)  | −8.0 (M)   | −5.0 (M)   | −12.0 (M)   | −9.0 (M)    | 2.0 (M)     | −5.0 (D)    |
| L = 3     | −32.0 (I)  | −20.0 (M)  | −17.0 (M)  | −14.0 (M)   | −12.0 (M)   | −9.0 (M)    | −7.0 (M)    |
| A = 0.3   |            |            |            |             |             |             |             |
| L = 0     | −11.5 (S0) | −1.5 (M1)  | −6.5 (M2)  | −13.5 (M0)  | −3.5 (M1)   | 0.5 (M2)    | −6.5 (D2)   |
| L = 1     | −20.5 (I)  | −10.5 (I)  | −7.5 (M)   | −12.5 (M)   | −12.5 (I)   | −8.5 (I)    | 3.5 (M)     |
| L = 2     | −32.5 (I)  | −22.5 (I)  | −19.5 (M)  | −16.5 (M)   | −21.5 (M)   | −20.5 (I)   | −8.5 (M)    |
| L = 3     | −44.5 (I)  | −34.5 (I)  | −31.5 (M)  | −28.5 (M)   | −25.5 (M)   | −30.5 (M)   | −20.5 (M)   |
| C = 1.2   |            |            |            |             |             |             |             |
| L = 0     | −17.5 (S0) | −7.5 (M0)  | −12.5 (M0) | −18.5 (M1)  | −9.5 (M0)   | −5.5 (M0)   | −2.5 (M1)   |
| L = 1     | −19.5 (I)  | −9.5 (I)   | 2.5 (M)    | −4.5 (D)    | −11.5 (I)   | −7.5 (I)    | −4.5 (I)    |
| L = 2     | −29.5 (I)  | −19.5 (I)  | −7.5 (I)   | −4.5 (M)    | −11.5 (M)   | −17.5 (I)   | −14.5 (M)   |
| L = 3     | −41.5 (I)  | −31.5 (I)  | −19.5 (M)  | −16.5 (M)   | −13.5 (M)   | −20.5 (M)   | −26.5 (M)   |
| T = 0.8   |            |            |            |             |             |             |             |
| L = 0     | −21.5 (S0) | −11.5 (M0) | −1.5 (M1)  | −8.5 (D1)   | −13.5 (M0)  | −9.5 (M0)   | −6.5 (M0)   |
| L = 1     | −25.5 (I)  | −15.5 (I)  | −5.5 (I)   | 6.5 (M)     | −0.5 (D)    | −7.5 (D)    | −10.5 (M)   |
| L = 2     | −37.5 (I)  | −27.5 (I)  | −17.5 (I)  | −5.5 (M)    | −2.5 (M)    | −9.5 (M)    | −16.5 (M)   |
| L = 3     | −49.5 (I)  | −39.5 (I)  | −29.5 (I)  | −17.5 (I)   | −14.5 (M)   | −11.5 (M)   | −18.5 (M)   |

-continued

|  | G | C | T | G | G | A |
|---|---|---|---|---|---|---|
| G = 1.5 | | | | | | |
| L = 0 | −29.0 (S0) | −19.0 (M0) | −9.0 (M0) | −1.0 (M1) | −8.0 (D1) | −15.0 (D1) | −14.0 (M0) |
| L = 1 | −31.0 (I) | −19.0 (M) | −11.0 (I) | −3.0 (I) | 9.0 (M) | 2.0 (M) | −5.0 (D) |
| L = 2 | −38.0 (I) | −26.0 (M) | −18.0 (I) | −10.0 (I) | 2.0 (M) | 14.0 (M) | 7.0 (D) |
| L = 3 | −50.0 (I) | −38.0 (M) | −30.0 (I) | −22.0 (I) | −10.0 (M) | 2.0 (M) | 5.0 (M) |
| A = 0.7 | | | | | | |
| L = 0 | −32.5 (S0) | −22.5 (M0) | −12.5 (M0) | −4.5 (M0) | 5.5 (M1) | 10.5 (M2) | 3.5 (D2) |
| L = 1 | −37.5 (I) | −27.5 (I) | −17.5 (I) | −9.5 (I) | 0.50 (I) | 5.5 (I) | 17.5 (M) |
| L = 2 | −49.5 (I) | −39.5 (I) | −29.0 (I) | −21.50 (I) | −11.5 (I) | −6.5 (I) | 5.5 (M) |
| L = 3 | −61.5 (I) | −51.5 (I) | −41.5 (I) | −33.50 (I) | −23.5 (I) | −18.5 (I) | −6.5 (M) |

As with the Smith-Waterman algorithm used above, to determine the alignment, a trajectory is traced back through the matrix working column-by-column and matrix-by-matrix, with the starting point being the cell with the highest value in the far right hand column of the last matrix. In this case, where a three-dimensional matrix is present, a path can be envisioned as being traced from one corner to the opposite, diagonal corner, for example, of a cube if all vectors were of equal length.

Here, beginning with the last matrix (corresponding to the last nucleotide flow), the highest value in the far right hand column is 17.5 (M), which is located in the L=1 row indicating that there is an A present. The M means that the next cell considered is the diagonally adjacent cell, which is 10.5 (M2). Being in row L=0, there is no nucleotide present but it indicates a move to the prior nucleotide matrix, in the same column ("G") but row L=2 because of the 2 after the M.

Now in the matrix where G=1.5, the beginning cell is in the second to last column on the right (same column as last matrix) in row L=2, which has a value of 14.0 (M). Thus, being in row L=2 infers that a homopolymer of length 2 is present for G. In other words, the alignment sequence contains GG and currently is: G G A. The M means that the next cell considered is the diagonally adjacent cell, which is 9.0 (M). This cell is in a "G" column and in L=1, thereby confirming the presence of two G's. The M again means that the next cell considered is the diagonally adjacent cell, which is −1.0 (M1) in row L=0. Thus, a move is made to the prior nucleotide matrix, in the same column ("T") but row L=1 because of the 1 after the M.

In the matrix where T=0.8, the beginning cell is in the "T" column, L=1 row, which has a value of 6.5 (M), indicating the presence of a T. Accordingly, at this point, the alignment sequence is: T G G A. The M means that the next cell considered is the diagonally adjacent cell, which is −1.5 (M1) in row L=0. Thus, a move is made to the prior nucleotide matrix, in the same column ("C") but row L=1 because of the 1 after the M.

In the matrix where C=1.2, the beginning cell is in the "C" column, L=1 row, which has a value of 2.5 (M), indicating the presence of a C. The M means that the next cell considered is the diagonally adjacent cell, which is −7.5 (M0) in row L=0. Thus, a move is made to the prior nucleotide matrix, in the same column ("G") but row L=0 because of the 0 after the M.

In the matrix where A=0.3, the beginning cell is in the "G" column at the far left, L=0 row, which has a value of −1.5 (M1). Because of the cell being in row L=0, no nucleotide is called out. However, a move is made to the prior nucleotide matrix, in the same column ("G") but row L=1 because of the 1 after the M.

In the matrix where G=1.4, the beginning cell is in row L=1, which has a value of 0.0 (M), indicating the presence of a G. The M means that the next cell considered is the diagonally adjacent cell, which is −10.0 (S0) in row L=0. Thus, a move is made to the prior nucleotide matrix, in the same column ("starting column") and row L=0 because of the 0 after the S.

In the matrix where T=0.2, the beginning cell is in row L=0, which has a value of −3.0 (S0) so no nucleobase is called. From here, a move back to the matrix where T=0.2, in the same column and row L=0, the cell has a value of −3.0 (S0). Again, no base call is made. Now, a move back to the matrix where C=0.3, in the same column and row L=0, the cell has a value of −2.0 (S0). Again, no base call is made. Finally, a move back to the matrix where A=0.1, in the same column and row L=0, the cell has a value of −0.5 (S0) and the opposite, diagonal corner of the three-dimensional matrix is reached.

In sum, the alignment of the putative nucleic acid sequence (based on the nucleotide flow order and signals from each flow) with a candidate reference nucleic acid sequence provides the sequence: G C T G G A, which accounts for the homopolymer stretch of GG in the sequence. As seen previously with the use of the Smith-Waterman algorithm alone, such a determination was not made.

In particular embodiments, an alignment module can receive data in SFF file format or FASTQ file format. The alignment module can store, transmit and/or output a sample nucleic acid sequences and related data and information in SAM or BAM file format.

Figure 6:
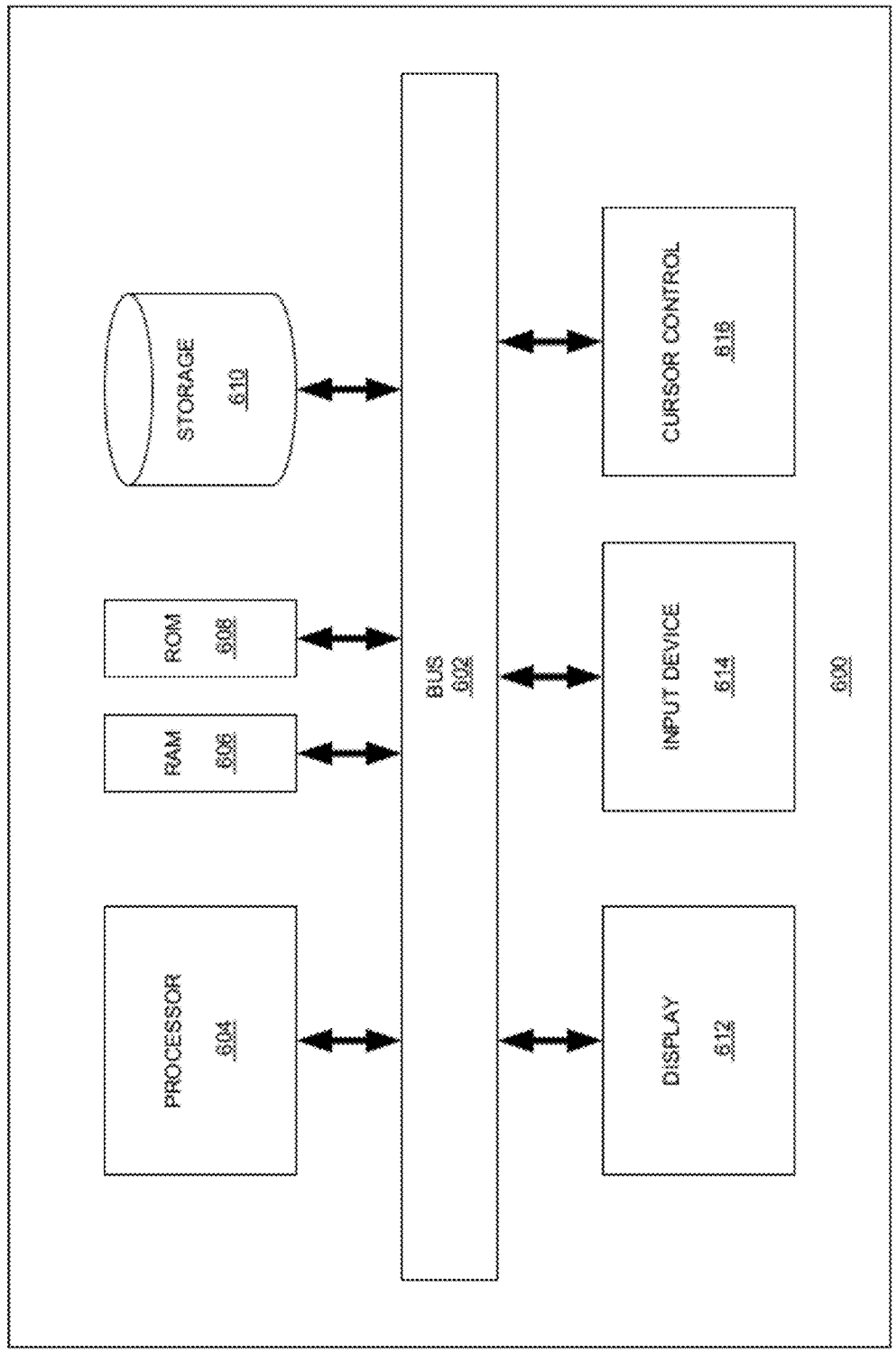
FIG. 6 is a block diagram that illustrates a computer system, in accordance with various embodiments.

FIG. 6 is a block diagram that illustrates a computer system 600, upon which embodiments of the present teachings can be implemented. Computer system 600 can include a bus 602 or other communication mechanism for communicating information, and a processor 604 coupled with bus 602 for processing information. Computer system 600 can also include a memory 606, which can be a random access memory (RAM) or other dynamic storage device, coupled to bus 602. Memory 606 can store data, such as sequence information, and instructions to be executed by processor 604. Memory 606 can also be used for storing temporary variables or other intermediate information during execution of instructions to be executed by processor 604. Computer system 600 can further include a read-only memory (ROM) 608 or other static storage device coupled to bus 602 for storing static information and instructions for processor 604. A storage device 610, such as a magnetic disk, an optical disk, a flash memory, or the like, can be provided and coupled to bus 602 for storing information and instructions.

Computer system 600 can be coupled by bus 602 to display 612, such as a cathode ray tube (CRT) or liquid crystal display (LCD), for displaying information to a computer user. An input device 614, such as a keyboard including alphanumeric and other keys, can be coupled to bus 602 for communicating information and commands to processor 604. Cursor control 616, such as a mouse, a trackball, a trackpad, or the like, can communicate direction information and command selections to processor 604, such as for controlling cursor movement on display 612. The input device can have at least two degrees of freedom in at least two axes that allows the device to specify positions in a plane. Other embodiments can include at least three degrees of freedom in at least three axes to allow the device to specify positions in a space. In additional embodiments, functions of input device 614 and cursor 616 can be provided by a single input devices such as a touch sensitive surface or touch screen.

Computer system 600 can perform the present teachings. Consistent with certain implementations of the present teachings, results are provided by computer system 600 in response processor 604 executing one or more sequences of one or more instructions contained in memory 606. Such instructions may be read into memory 606 from another computer-readable medium, such as storage device 610. Execution of the sequences of instructions contained in memory 606 can cause processor 604 to perform the processes described herein. Alternatively, hard-wired circuitry may be used in place of or in combination with software instructions to implement the present teachings. Thus, implementations of the present teachings are not limited to any specific combination of hardware circuitry and software.

The term "computer-readable medium" as used herein refers to any media that participates in providing instructions to processor 604 for execution. Such a medium may take many forms, including but not limited to, nonvolatile memory, volatile memory, and transmission media. Nonvolatile memory includes, for example, optical or magnetic disks, such as storage device 610. Volatile memory includes dynamic memory, such as memory 606. Transmission media includes coaxial cables, copper wire, and fiber optics, including the wires that comprise bus 602. Non-transitory computer readable medium can include nonvolatile media and volatile media.

Common forms of non-transitory computer readable media include, for example, floppy disk, flexible disk, hard disk, magnetic tape, or any other magnetic medium, a CD-ROM, any other optical medium, punch cards, paper tape, any other physical medium with patterns of holes, a RAM, a PROM, an EPROM, a FLASH-EPROM, and other memory chips or cartridge or any other tangible medium from which the computer can read.

Various forms of computer readable media may be involved in carrying one or more sequences of one or more instructions to processor 604 for execution. For example the instructions may initially be stored on the magnetic disk of a remote computer. The remote computer can load the instructions into its dynamic memory and send instructions over a network to computer system 600. A network interface coupled to bus 602 can receive the instructions and place the instructions on bus 602. Bus 602 can carry the instructions to memory 606, from which processor 604 can retrieve and execute the instructions. Instructions received by memory 606 may optionally be stored on storage device 610 either before or after execution by processor 604.

The execution of any of the methods of nucleic acid sequencing analysis described herein, where appropriate, can be carried out by an appropriately programmed computer system. In terms of hardware architecture, the computer generally includes a processor, memory, and one or more input and/or output (I/O) devices (or peripherals) that are communicatively coupled via a local interface. The local interface can be, for example, one or more buses or other wired or wireless connections, as is known in the art. The local interface can have additional elements, which are omitted for simplicity, such as controllers, buffers (caches), drivers, repeaters and receivers, to enable communications. Further, the local interface can include address, control, and/or data connections to enable appropriate communications among the other computer components.

A processor is a hardware device for executing software, particularly software stored in memory. The processor can be any custom made or commercially available processor, a central processing unit (CPU), an auxiliary processor among several processors associated with the computer, a semiconductor based microprocessor (in the form of a microchip or chip set), a macroprocessor, or generally any device for executing software instructions. Examples of suitable commercially available microprocessors include: a PA-RISC series microprocessor from Hewlett-Packard Company, an 80x86 or Pentium series microprocessor from Intel Corporation, a PowerPC microprocessor from IBM, a Sparc microprocessor from Sun Microsystems, Inc., and a 68xxx series microprocessor from Motorola Corporation. A processor can also represent a distributed processing architecture.

Memory can include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, memory can incorporate electronic, magnetic, optical, and/or other types of storage media. Memory can have a distributed architecture where various components are situated remote from one another, but are still accessed by the processor.

The software in memory can include one or more separate programs. The separate programs can comprise ordered listings of executable instructions for implementing logical functions. In some embodiments, the software in memory includes a system for identifying data streams in accordance with the present teachings and a suitable operating system (O/S). A non-exhaustive list of examples of suitable commercially available operating systems includes: (a) a Windows operating system available from Microsoft Corporation; (b) a Netware operating system available from Novell, Inc.; (c) a Macintosh operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; and (f) an appliance-based operating system, such as that implemented in handheld computers or personal digital assistants (PDAs) (e.g., PalmOS available from Palm Computing, Inc., and Windows CE available from Microsoft Corporation). The operating system essentially controls the execution of other computer programs such as the system, and provides scheduling, input-output control, file and data management, memory management, and communication control and related services.

The system for identifying data streams can be a source program, executable program (object code), script, or any other entity comprising a set of instructions to be performed. When a source program, the program can be translated via a compiler, assembler, interpreter, or the like, which may or may not be included within the memory, so as to operate properly in connection with the O/S. Furthermore, the system for identifying data streams can be written as (a) an object oriented programming language, which has classes of data and methods, or (b) a procedural programming language, which has routines, subroutines, and/or functions, for example but not limited to, C, C++, Pascal, Basic, Fortran, Cobol, Perl, Java, and Ada. In certain embodiments, the system for identifying data streams is written in C++. In various embodiments, the system for identifying data streams is created using Power Builder. The I/O devices can include input devices, for example, a keyboard, a mouse, a scanner, a microphone, a touch screen, an interface for various medical devices, a bar code reader, a stylus, a laser reader, a radio-frequency device reader, and the like. Furthermore, the I/O devices also can include output devices, for example, a printer, a bar code printer, a display, and the like. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, and the like.

If the computer is a PC, workstation, PDA, or the like, the software in the memory can include a basic input output system (BIOS). The BIOS is a set of essential software routines that initialize and test hardware at startup, start the O/S, and support the transfer of data among the hardware devices. The BIOS is stored in ROM so that the BIOS can be executed when the computer is activated.

When computer is in operation, the processor is configured to execute software stored within memory, to communicate data to and from memory, and generally to control operations of the computer pursuant to the software. The system for identifying data streams and the O/S, in whole or in part, but typically the latter, are read by a processor, perhaps buffered within the processor, and then executed.

When the system is implemented in software, it should be noted that the system can be stored on any computer readable medium for use by or in connection with any computer-related system or method. The system for identifying data streams can be embodied in any computer-readable medium for use by or in connection with an instruction execution system, apparatus or device, such as a computer-based system, processor-containing system, or other system that can fetch the instructions from the instruction execution system, apparatus or device and execute the instructions.

As used herein, a "computer-readable medium" can be any means that can store, communicate, propagate, or transport the program for use by or in connection with the instruction execution system, apparatus, or device. For example, a "computer readable medium" can be an electronic, magnetic, optical, or other physical device or means that can contain or store a computer program for use by or in connection with a computer-related system or method. The computer readable medium can be, for example, an electronic, magnetic, optical, electromagnetic, infrared, or semiconductor system, apparatus, device, or propagation medium. More specific examples of a computer-readable medium include: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner, if necessary, and then stored in a computer memory.

In particular embodiments, where the system for identifying data streams is implemented in hardware, a system for identifying data streams can be implemented with any, or a combination of, the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), and the like.

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Figure 7:
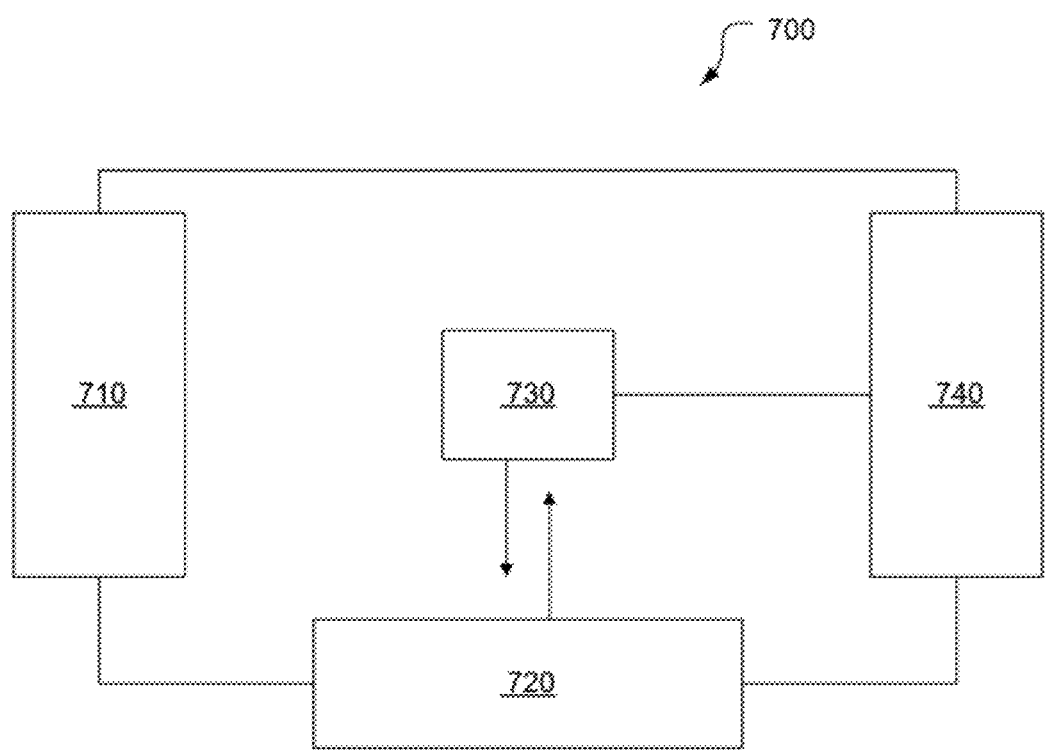
FIG. 7 is a block diagram that illustrates a system for determining a nucleic acid sequence, in accordance with various embodiments.

Various embodiments of nucleic acid sequencing platforms, such as a nucleic acid sequencer, can include components as displayed in the block diagram of FIG. 7. According to various embodiments, sequencing instrument 700 can include a fluidic delivery and control unit 702, a sample processing unit 704, a signal detection unit 706, and a data acquisition, analysis and control unit 708. Various embodiments of instrumentation, reagents, libraries and methods used for next generation sequencing are described in U.S. Patent Application Publication Nos. 2009/0127589 and 2009/0026082 are incorporated herein by reference. Various embodiments of instrument 700 can provide for automated sequencing that can be used to gather sequence information from a plurality of sequences in parallel, such as substantially simultaneously.

In various embodiments, the fluidics delivery and control unit 702 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 704 can include a sample chamber, such as flow cell, a substrate, a micro-array, a multi-well tray, or the like. The sample processing unit 704 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 706 can include an imaging or detection sensor. For example, the imaging or detection sensor can include a CCD, a CMOS, an ion or chemical sensor, such as an ion sensitive layer overlying a CMOS or FET, a current or voltage detector, or the like. The signal detection unit 706 can include an excitation system to cause a probe, such as a fluorescent dye, to emit a signal. The excitation system can include an illumination source, such as arc lamp, a laser, a light emitting diode (LED), or the like. In particular embodiments, the signal detection unit 706 can include optics for the transmission of light from an illumination source to the sample or from the sample to the imaging or detection sensor. Alternatively, the signal detection unit 706 may provide for electronic or non-photon based methods for detection and consequently not include an illumination source. In various embodiments, electronic-based signal detection may occur when a detectable signal or species is produced during a sequencing reaction. For example, a signal can be produced by the interaction of a released byproduct or moiety, such as a released ion, such as a hydrogen ion, interacting with an ion or chemical sensitive layer. In other embodiments a detectable signal may arise as a result of an enzymatic cascade such as used in pyrosequencing (see, for example, U.S. Patent Application Publication No. 2009/0325145, the entirety of which being incorporated herein by reference) where pyrophosphate is generated through base incorporation by a polymerase which further reacts with ATP sulfurylase to generate ATP in the presence of adenosine 5' phosphosulfate wherein the ATP generated may be consumed in a luciferase mediated reaction to generate a chemiluminescent signal. In another example, changes in an electrical current can be detected as a nucleic acid passes through a nanopore without the need for an illumination source.

In various embodiments, a data acquisition analysis and control unit 708 can monitor various system parameters. The system parameters can include temperature of various portions of instrument 700, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 700 can be used to practice variety of sequencing methods including ligation-based methods, sequencing by synthesis, single molecule methods, nanopore sequencing, and other sequencing techniques.

In various embodiments, the sequencing instrument 700 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 700 can obtain the sequence information from a single nucleic acid molecule or from a group of substantially identical nucleic acid molecules.

In various embodiments, sequencing instrument 700 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

EXAMPLES

Figure 8:
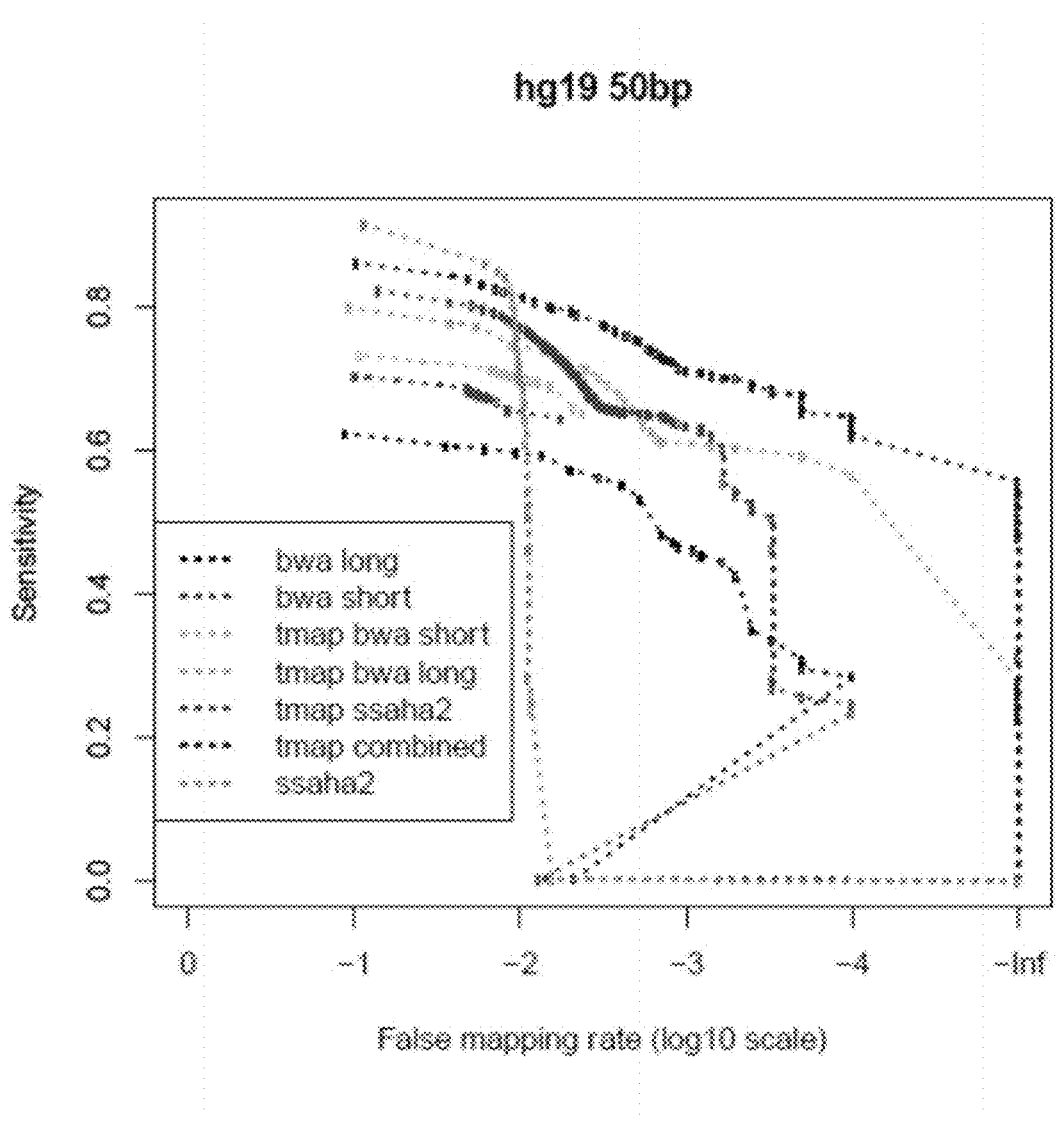
FIG. 8 is a graph illustrating the mapping sensitivity and false mapping rate.

FIG. 8 is a graph comparing the sensitivity and false mapping rate (specificity) for various mapping methods. A simulated dataset is generated with 50 bp read lengths. The reads of the simulated dataset are mapped using various algorithms ("bwa-short", "bwa-long", "ssaha", "tmap bwa short", "tmap bwa long", "tmap ssaha2", and "tmap combined"). "bwa-short" is as described in Li, H, Durbin, R (2009). Fast and accurate short read alignment with Burrows-Wheeler transform. *Bioinformatics*, 25, 14:1754-60. "bwa-long" is as described in Li, H, Durbin, R (2010) Fast and accurate long-read alignment with Burrows-Wheeler transform. *Bioinformatics*, 26, 5:589-95. "ssaha2" is as described in Ning et al. (2001) SSAHA: a fast search method for large DNA databases. *Genome Res.* 11, 10:1725-9.

"tmap bwa short" is the BWA short algorithm modified according to various embodiments of the present teaching. "tmap bwa long" is the BWA long algorithm modified according to various embodiments of the present teaching. "tmap ssaha2" is the SSAHA algorithm modified according to various embodiments of the present teaching. "tmap combined" combines the results of "tmap bwa short", "tmap bwa long", and "tmap ssaha2" according to various embodiments of the present teaching.

What is claimed is:

1. A computer implemented method of aligning nucleic acid sequence information for at least one of a sample nucleic acid template against a candidate reference nucleic acid sequence, the method comprising:

flowing a series of nucleotide flows to a plurality of defined spaces resulting in one or more nucleotide incorporate events detecting a plurality of signals from the defined spaces corresponding the one or more nucleotide incorporation events;

identifying a candidate nucleic acid sequence based upon the plurality of signals and respective nucleobases associated with respective flows of the series of nucleotide flows;

mapping the candidate nucleic acid sequence to a reference genome to determine a reference nucleic acid sequence;

forming, for one or more nucleobases of the series of nucleotide flows, a matrix of cells comprising a first dimension corresponding to the nucleobases of the reference nucleic acid sequence and a second dimension comprising homopolymer lengths from 0 to n for homopolymeric incorporations of nucleobases associated with respective nucleotide flows;

calculating a value for selected cells of the matrix reflecting the overlap of the nucleobase of the nucleotide flow with nucleobases of the reference nucleic acid sequence using a local sequence alignment method;

weighting the values of the matrix based upon the respective signal of the nucleobase of the nucleotide flow;

traversing the matrix to determine an aligned nucleic acid sequence; and outputting the aligned nucleic acid sequence.

2. The method of claim 1 wherein mapping to determine a reference nucleic acid sequence comprises determining more than one reference nucleic acid sequence and the steps of forming, calculating, weighting and tracing are performed for the additional reference nucleic acid sequences.

3. The method of claim 1 wherein each of the series of signals is indicative of a hydrogen ion concentration in the defined space.

4. The method of claim 1 wherein calculating the value for cells of the matrix comprises scoring an alignment.

5. The method of claim 4 wherein scoring an alignment comprises setting a match parameter value, a non-match parameter value, and a gap parameter value.

6. The method of claim 1 wherein the local sequence alignment method is a Smith-Waterman algorithm.

7. The method of claim 6 wherein the local sequence alignment method comprises determining the maximum of:

$Cell_{i-1,j-1}$+a score, $Cell_{i-1,j}$+a first gap penalty, and $Cell_{i,j-1}$+a second gap penalty, wherein i is the position along the first dimension and j is the position along the second dimension.

8. The method of claim 1 wherein weighting is performed by a function in response to the difference between a measured signal for a nucleobase of the series of nucleotide flows and an estimated value of that nucleobase.

9. The method of claim 1 wherein weighting is performed by a function in response to a homopolymer number.

10. The method of claim 9 wherein the function is abs (homopolymer number−measured signal)*a penalty.

11. A non-transitory computer-readable medium having computer readable instructions stored thereon for execution by a processor, the instructions comprising:

instructions for flowing a series of nucleotide flows to a plurality of defined spaces resulting in one or more nucleotide incorporation events;

instructions for detecting a plurality of signals from the defined spaces corresponding the one or more nucleotide incorporation events;

instructions for identifying a candidate nucleic acid sequence based upon the plurality of signals and respective nucleobases associated with respective flows of the series of nucleotide flows;

instructions for mapping the candidate nucleic acid sequence to a reference genome to determine a reference nucleic acid sequence;

instructions for forming, for one or more nucleobases of the series of nucleotide flows, a matrix of cells comprising a first dimension corresponding to the nucleobases of the reference nucleic acid sequence and a second dimension comprising homopolymer lengths from 0 to n for homopolymeric incorporations of nucleobases associated with respective nucleotide flows;

instructions for calculating a value for selected cells of the matrix reflecting the overlap of the nucleobase of the nucleotide flow with nucleobases of the reference nucleic acid sequence using a local sequence alignment method;

instructions for weighting the values of the matrix based upon the respective signal of the nucleobase of the nucleotide flow; and instructions for traversing the matrix to determine an aligned nucleic acid sequence.

12. The method of claim 11 wherein the series of signals are indicative of a hydrogen ion concentration in the defined space.

13. The method of claim 11 wherein the local sequence alignment method is a Smith-Waterman algorithm.

14. The method of claim 13 wherein the local sequence alignment method comprises determining the maximum of:

$Cell_{i-1,j-1}$+a score, $Cell_{i-1,j}$+a first gap penalty, and $Cell_{i,j-1}$+a second gap penalty, wherein i is the position along the first dimension and j is the position along the second dimension.

15. A system for nucleic acid sequence analysis, the system comprising:

an aligner module configured to perform the steps of:

generating a nucleic acid sequence information for at least one sample nucleic acid template disposed in one or more of a plurality of defined spaces based on a series of nucleotide flows introduced to the defined spaces resulting in one or more nucleotide incorporation events detected as a series of signals associated with the defined spaces;

identifying a candidate nucleic acid sequence based upon the plurality of signals and respective nucleobases associated with respective flows of the series of nucleotide flows;

mapping the candidate nucleic acid sequence to a reference genome to determine a reference nucleic acid sequence;

forming, for selected nucleobases of the series of nucleotide flows, a matrix of cells comprising a first dimension corresponding to the nucleobases of the candidate reference nucleic acid sequence and a second dimension comprising homopolymer lengths from 0 to n for homopolymeric incorporations of nucleobases associated with respective nucleotide flows;

calculating a value for selected cells of the matrix reflecting the overlap of the nucleobase of the nucleotide flow with nucleobases of the reference nucleic acid sequence using a local sequence alignment method;

weighting the values of the matrix based upon the respective signal of the nucleobase of the nucleotide flow; and traversing the matrix to determine an aligned nucleic acid sequence.

16. The method of claim 15 wherein the series of signals are indicative of a hydrogen ion concentration in the defined space.

17. The method of claim 15 wherein weighting is performed by a function in response to a homopolymer number.

* * * * *